US010041111B2

(12) United States Patent
Park et al.

(10) Patent No.: US 10,041,111 B2
(45) Date of Patent: Aug. 7, 2018

(54) METHOD FOR DETECTING AND QUANTIFYING BIOMATERIALS BY USING ACTIVITY OF NUCLEIC ACID POLYMERASE REGULATED BY TARGET MATERIAL

(71) Applicant: Korea Advanced Institute of Science and Technology, Daejeon (KR)

(72) Inventors: Hyun Gyu Park, Daejeon (KR); Ki Soo Park, Daejeon (KR); Chang Yeol Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/524,093

(22) PCT Filed: Nov. 4, 2015

(86) PCT No.: PCT/KR2015/011817
§ 371 (c)(1),
(2) Date: May 3, 2017

(87) PCT Pub. No.: WO2016/072758
PCT Pub. Date: May 12, 2016

(65) Prior Publication Data
US 2017/0335381 A1    Nov. 23, 2017

(30) Foreign Application Priority Data

Nov. 4, 2014 (KR) .................. 10-2014-0152468

(51) Int. Cl.
*C12Q 1/68* (2018.01)
*C12N 15/115* (2010.01)
*C12Q 1/6851* (2018.01)

(52) U.S. Cl.
CPC .......... *C12Q 1/6851* (2013.01); *C12N 15/115* (2013.01); *C12N 2310/16* (2013.01)

(58) Field of Classification Search
USPC ............ 435/6.6, 6.11, 91.1, 91.31, 6.1, 6.13, 435/91.2, 287.2; 424/9.1; 536/23.1, 536/24.5, 23.5, 24.1, 24.31
See application file for complete search history.

(56) References Cited

U.S. PATENT DOCUMENTS 5,660,985 A    8/1997 Pieken et al.
2012/0035065 A1    2/2012 Smolke et al.

FOREIGN PATENT DOCUMENTS

| JP | 5404620 B2 | 2/2014 |
| KR | 10-2009-0067334 A | 6/2009 |
| KR | 10-2014-0029825 A | 3/2014 |
| KR | 10-2014-0119602 A | 10/2014 |

OTHER PUBLICATIONS

Friedrichs et al, ChemBioChem, vol. 8, pp. 1662-1666 (2007).*
Cotten, M., et al., "2'-O-methyl, 2'-O-ethyl oligoribonucleotides and phosphorothioate oligodeoxyribonucleotides as inhibitors of the in vitro U7 snRNP-dependent mRNA processing event", "Nucleic Acids Research", May 25, 1991, pp. 2629-2635, vol. 19.
Dang, C., et al., "Oligonucleotide Inhibitors of Taq DNA Polymerase Facilitate Detection of Low Copy Number Targets by PCR", "Journal of Molecular Biology", 1996, pp. 268-278, vol. 264.
Ellington, A.D., et al., "In vitro selection of RNA molecules that bind specific ligands", "Nature", Aug. 30, 1990, pp. 818-822, vol. 346.
Friedrichs, E., et al., "Controlling DNA Polymerization with a Switchable Aptamer", "ChemBioChem", 2007, pp. 1662-1666, vol. 8.
Gianneschi, N.C., et al., "Design of Molecular Logic Devices Based on a Programmable DNA-Regulated Semisynthetic Enzyme", "Angewandte Chemie International Edition", 2007, pp. 3955-3958, vol. 46.
Hobbs, J., et al., "Polynucleotides containing 2'-amino-2'-deoxyribose and 2'-azido-2'-deoxyribose", "Biochemistry", Dec. 4, 1973, pp. 5138-5145, vol. 12, No. 25.
Hutter, E., et al., "Gold-nanoparticle-based biosensors for detection of enzyme activity", "Trends in Pharmacological Sciences", Sep. 2013, pp. 497-507, vol. 34, No. 9.
Lin, Y., et al, "Inhibition of Multiple Thermostable DNA Polymerases by a Heterodimeric Aptamer", "Journal of Molecular Biology", 1997, pp. 100-111, vol. 271.
Masuko, M., et al., "Optimization of excimer-forming two-probe nucleic acid hybridization method with pyrene as a fluorophore", "Nucleic Acids Research", 1998, pp. 5409-5416, vol. 26, No. 23.
Niemeyer, C.M., "Semisynthetic DNAProtein Conjugates for Biosensing and Nanofabrication", "Angewandte Chemie International Edition", 2010, pp. 1200-1216, vol. 49.
Ono, T., et al., "Direct Fluorescence Monitoring of DNA Base Excision Repair", "Angewandte Chemie International Edition in English", Feb. 13, 2012, pp. 1689-1692, vol. 51, No. 7.
Park, J.-W., et al., "Immobilization-free screening of aptamers assisted by graphene oxide", "Chemical Communications", Feb. 18, 2012, pp. 2071-2073, vol. 48, No. 15.

(Continued)

*Primary Examiner* — Jane Zara
(74) *Attorney, Agent, or Firm* — Hultquist, PLLC; Steven J. Hultquist

(57) ABSTRACT

The present invention relates to a method of detecting and quantifying biomolecules using nucleic acid polymerase activity controlled by the target molecule, and more particularly to a method for detecting or quantifying biomolecules, which can detect and quantify nucleic acids, proteins, small-molecular substances, physiologically active substances (enzymatic activities), etc., with high sensitivity, based on the change in DNA polymerase activity caused by specific binding of a specific nucleic acid that forms a complex with a DNA aptamer prepared so as to comprise a single-stranded DNA that specifically recognizes the specific nucleic acid. The present invention can provide a method for diagnosing biomolecules, which can detect and quantify target nucleic acids, target proteins, target small-molecular substances, target enzyme activities and the like in a label-free and sensitive manner by controlling polymerase activity through target molecule-induced conformational change of a DNA aptamer.

43 Claims, 10 Drawing Sheets
(9 of 10 Drawing Sheet(s) Filed in Color)

(56) References Cited

OTHER PUBLICATIONS

Pavlov, V., et al., "Fluorescence Detection of DNA by the Catalytic Activation of an Aptamer/Thrombin Complex", "Journal of the American Chemical Society", Apr. 15, 2005, pp. 6522-6523, vol. 127.
Saghatelian, A., et al., "DNA Detection and Signal Amplification via an Engineered Allosteric Enzyme", "Journal of the American Chemical Society", 2003, pp. 344-345, vol. 125.
Song, S., et al., "Gold-Nanoparticle-Based Multicolor Nanobeacons for Sequence-Specific DNA Analysis", "Angewandte Chemie International Edition", 2009, pp. 8670-8674, vol. 48.
Sproat, B., et al., "New synthetic routes to synthons suitable for 2'-O-allyloligoribonucleotide assembly", "Nucleic Acids Research", Feb. 25, 1991, pp. 733-738, vol. 19, No. 4.
Tuerk, C., et al., "Systematic Evolution of Ligands by Exponential Enrichment: RNA Ligands to Bacteriophage T4 DNA Polymerase", "Science", Aug. 3, 1990, pp. 505-510, vol. 249.
Tyagi, S., et al., "Molecular Beacons: Probes that Fluoresce upon Hybridization", "Nature Biotechnology", Mar. 1996, pp. 303-308, vol. 14.
Wu, C.-S., et al., "Robust silica-coated quantum dotmolecular beacon for highly sensitive DNA detection", "Biosensors and Bioelectronics", Mar. 5, 2011, pp. 3870-3875, vol. 26.
Yakimovich, O.Y., et al., "Influencle of DNA Aptamer Structure on the Specifity of Binding to Taq DNA Polymerase", "Biochemistry (Moscow)", 2003, pp. 228-235, vol. 68, No. 2.
Yeh, H.-C., et al., "A DNA-Silver Nanocluster Probe That Fluoresces upon Hybridization", "Nano Letters", Jul. 19, 2010, pp. 3106-3110, vol. 10.

\* cited by examiner

[fig.1]
(1) Target Recognition
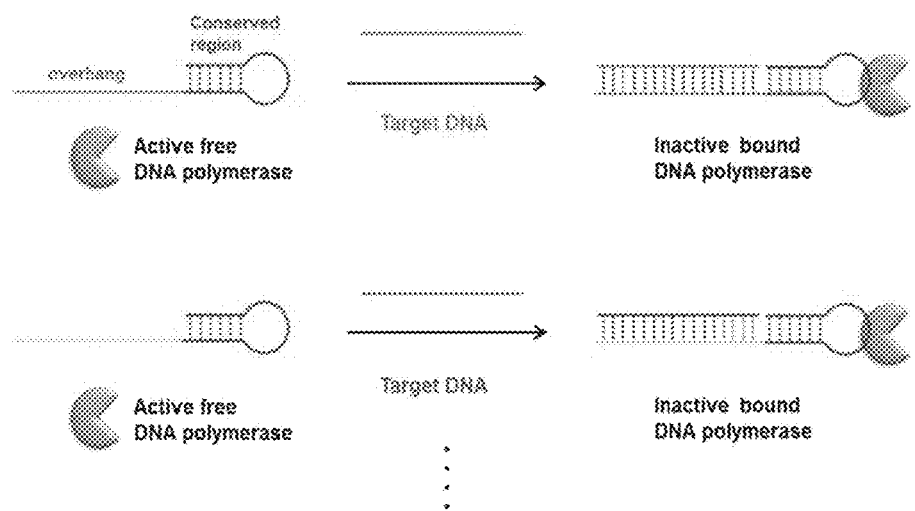
(2) Signal Transduction
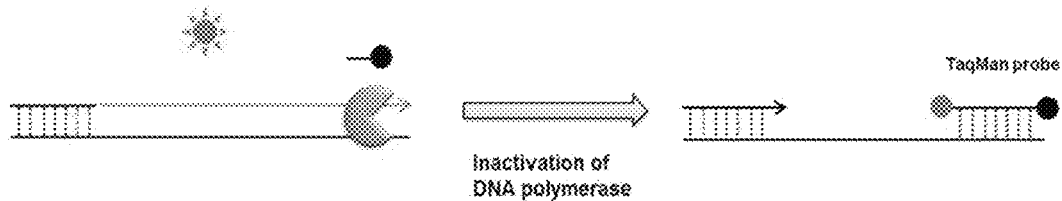

[fig.2]
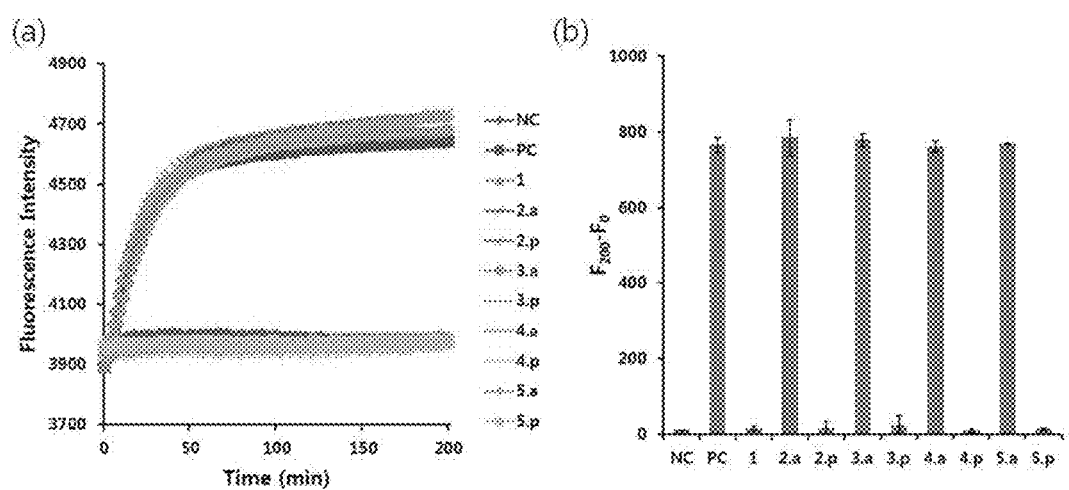
[fig.3]
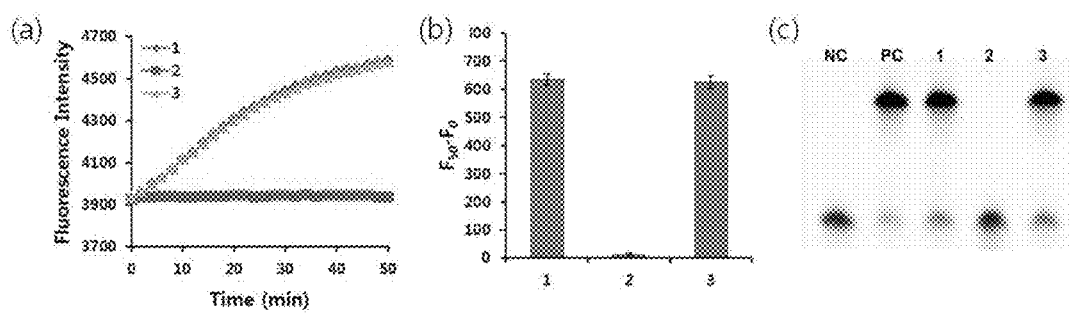

[fig.4]
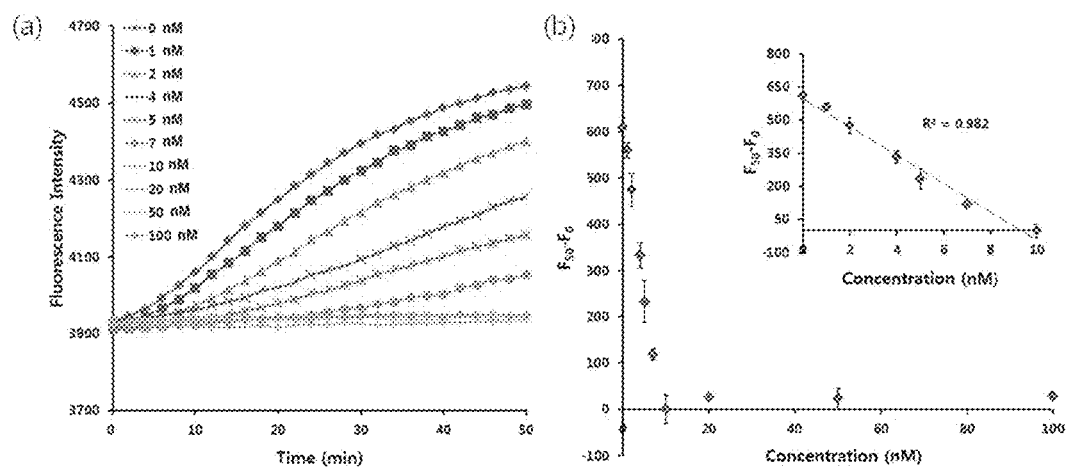
[fig.5]
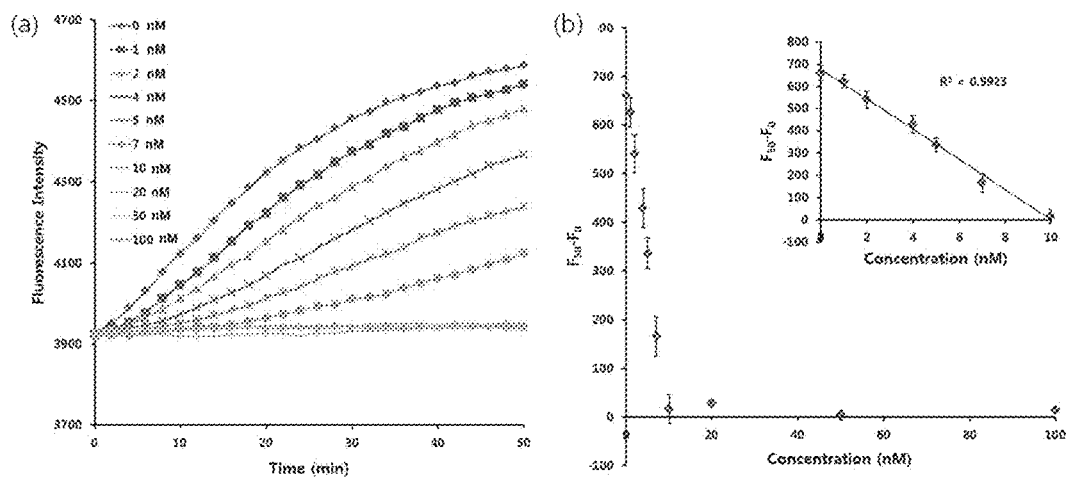

[fig.6]
(1) Target Recognition
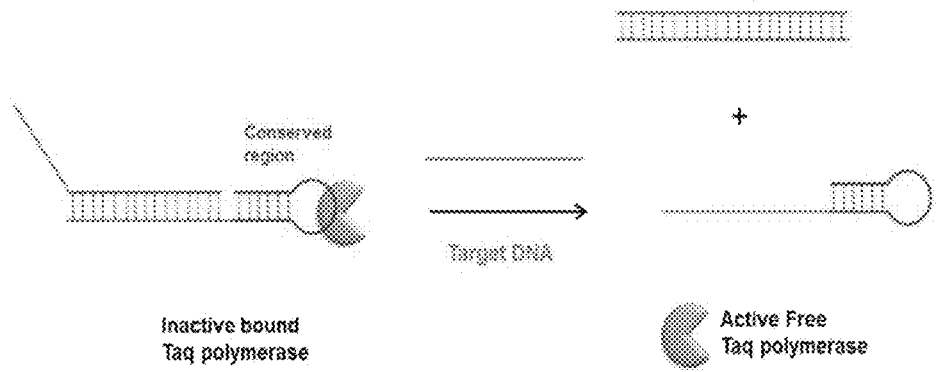
(2) Signal transduction
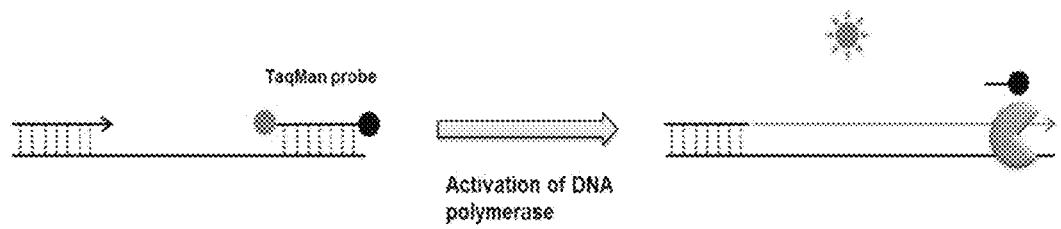

[fig.7]
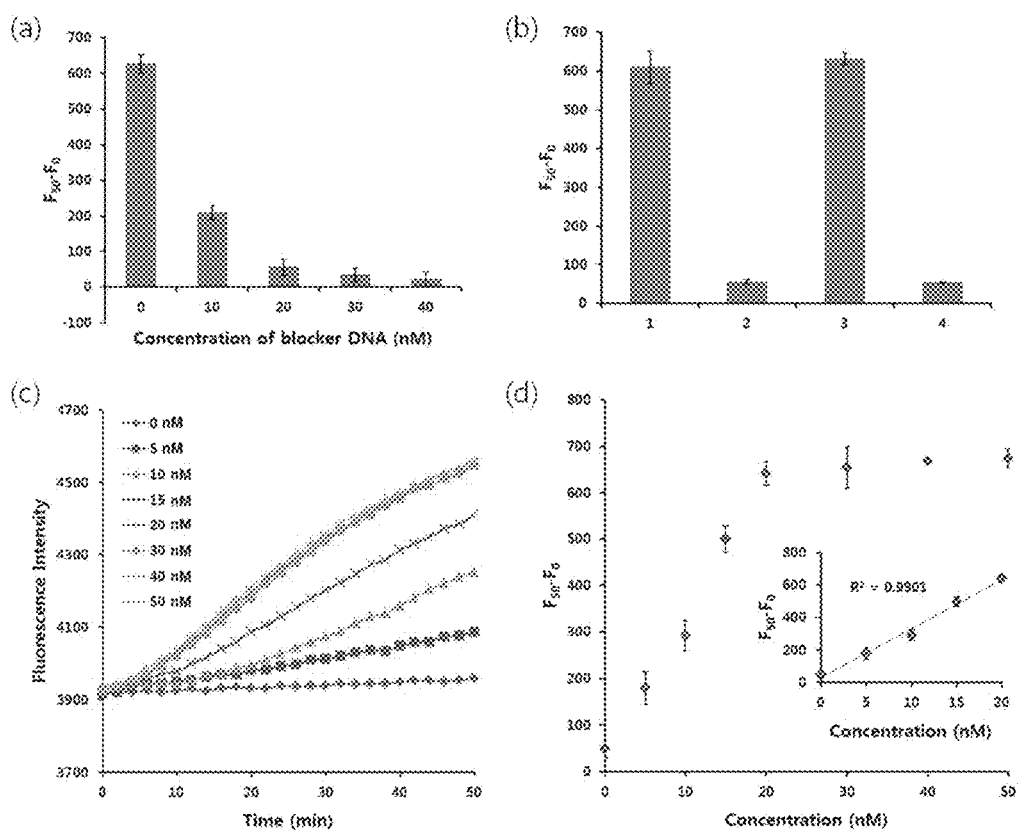

[fig.8]
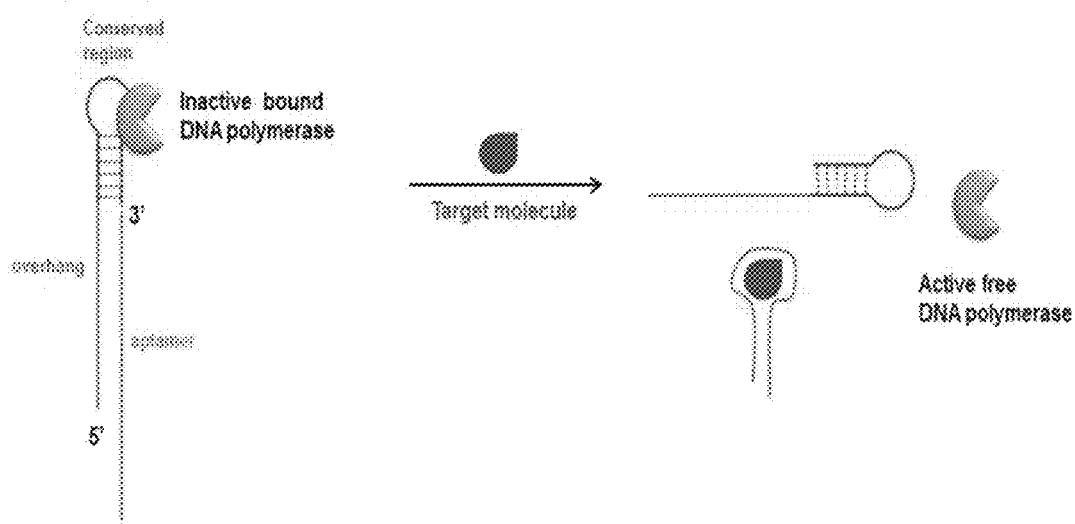
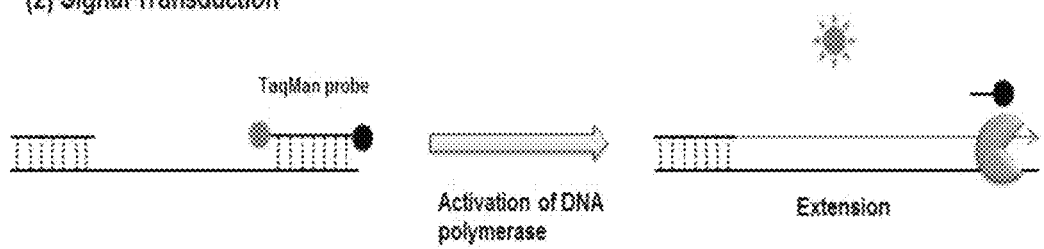

[fig.9]
(1) Target recognition of UDG
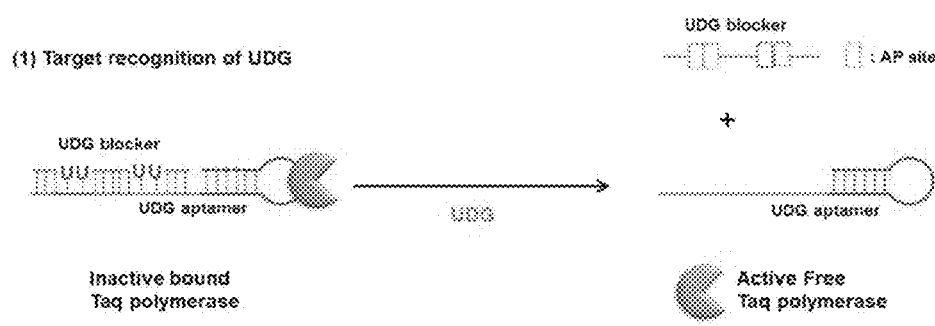
(2) Signal Transduction
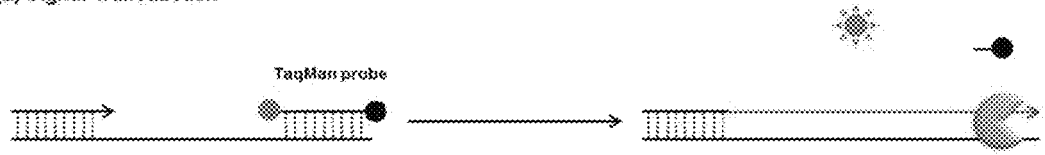

[fig.10]
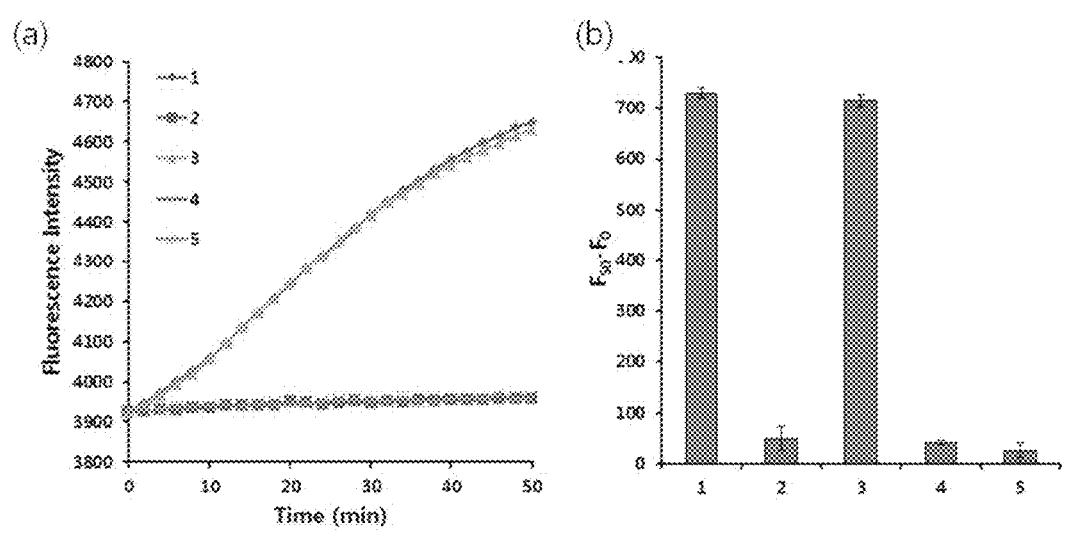

[fig.11]
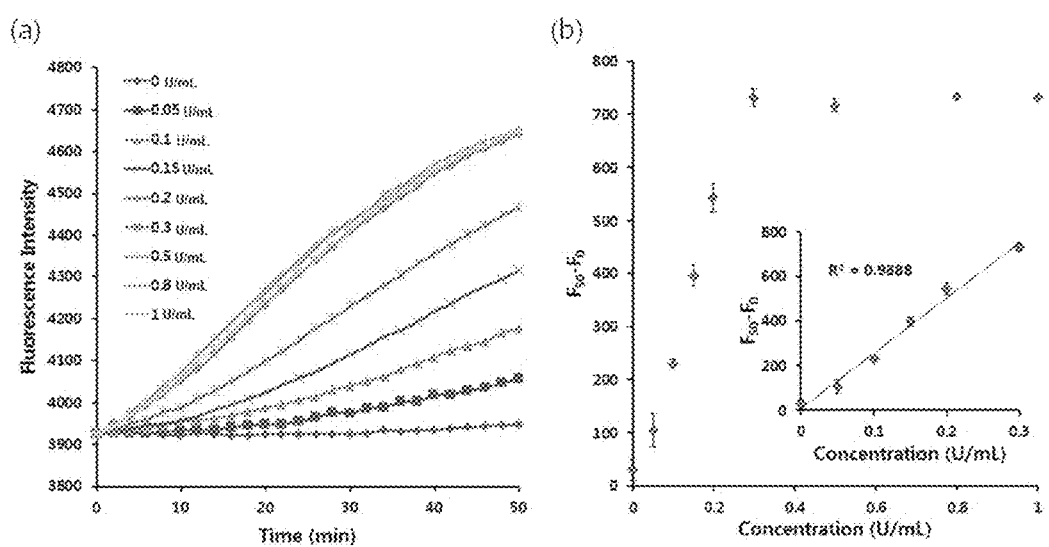

[fig.12]
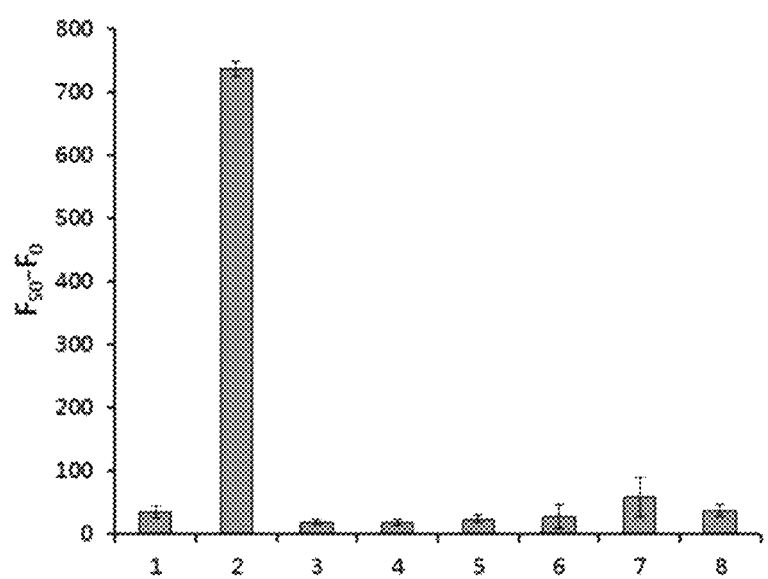

METHOD FOR DETECTING AND QUANTIFYING BIOMATERIALS BY USING ACTIVITY OF NUCLEIC ACID POLYMERASE REGULATED BY TARGET MATERIAL

CROSS-REFERENCE TO RELATED APPLICATIONS

This application is a U.S. national phase under the provisions of 35 U.S.C. § 371 of International Patent Application No. PCT/KR2015/011817 filed Nov. 4, 2015, which in turn claims priority of Korean Patent Application No. 10-2014-0152468 filed Nov. 4, 2014. The disclosures of such international patent application and Korean priority patent application are hereby incorporated herein by reference in their respective entireties, for all purposes.

TECHNICAL FIELD

The present invention relates to a method of detecting and quantifying biomolecules using nucleic acid polymerase activity controlled by the target molecule, and more particularly to a method for detecting or quantifying biomolecules, which can detect and quantify nucleic acids, proteins, small-molecular substances, physiologically active substances (enzymatic activities), etc., with high sensitivity, based on the change in DNA polymerase activity caused by specific binding of a specific nucleic acid that forms a complex with a DNA aptamer prepared so as to comprise a single-stranded DNA that specifically recognizes the specific nucleic acid.

BACKGROUND ART

Nucleic acid-based detection technologies play an important role in disease diagnosis, drug detection, environmental monitoring and criminal investigation, and there has been a continued need for new detection technologies which have excellent sensitivity and specificity and which are convenient to use. A nucleic acid-based detection technology, which has been typically used in the prior art, is based on a molecular beacon which is a U-shaped DNA probe labeled with a fluorophore and a quencher. This technology comprises confirming whether a fluorescent signal is produced by the conformational change of the molecular beacon due to the presence of a target nucleic acid (Tyagi et al., *Nature biotechnology*, 14:303-308, 1996; Masuko et al., *Nucleic Acids Research*, 26:5409-5416, 1998). Because this technology can rapidly analyze a target nucleic acid without isolating nucleic acids, it is widely used, and various types of molecular beacon-based nucleic acid analysis technologies have been developed (Song et al., *Angewandte Chemie-International Edition*, 48:8670-8674, 2009; Wu et al., *Biosensors & Bioelectronics*, 26:3870-3875, 2011; Yeh et al., *Nano Letters*, 10:3870-3875, 2011). However, the above-mentioned molecular beacon-based analysis technology has a shortcoming in that, because a target nucleic acid and a molecular beacon react at a ratio of 1:1 to generate a fluorescent signal, it is difficult to achieve high sensitivity.

In recent years, for the purposes of overcoming this problem and developing a detection sensor having excellent sensitivity, attempts have been made to use enzyme as a tool for signal amplification. A typical example includes a system in which an enzyme labeled with a detection probe for detecting a target nucleic acid and with an inhibitor is introduced (Gianneschi et al., *Angewandte Chemie-International Edition*, 46: 3955-3958, 2007; Saghatelian et al., *Journal of the American Chemical Society*, 125: 344-345, 2003; Pavlov et al., *Journal of the American Chemical Society*, 127: 6522-6523, 2005; Niemeyer et al., *Angewandte Chemie-International Edition*, 49: 1200-1216, 2010). In this system, the presence of the target nucleic acid blocks the inhibitory function of the inhibitor through hybridization with the detection probe, and the restored enzymatic activity generates a high fluorescent signal. However, this technology has shortcomings in that it requires a process of labeling the enzyme with the inhibitor, is time-consuming, and requires great skill. Furthermore, it has a shortcoming in that the labeling process itself may cause a conformational change of the enzyme to reduce the activity of the enzyme. In addition, this technology has a limitation in that it is hardly used as a versatile technology for detection of various target nucleic acids, because it is required to prepare an enzyme-inhibitor complex for each target nucleic acid. Thus, it is demanded to develop a label-free, enzyme-based universal for detection of various target nucleic acids.

Accordingly, the present inventors have made extensive efforts to overcome the above-described problems occurring in the prior art and to develop a highly sensitive enzyme-based detection and quantification system which does not need to be labeled with an inhibitor and which can be universally used for the detection and quantification of various target nucleic acids. As a result, the present inventors have found that the use of a DNA aptamer comprising a single-stranded DNA that specifically recognizes a target nucleic acid enables the following in a selective and accurate way, thereby completing the present invention: (1) detection and quantification of a target nucleic acid in switch-off mode; (2) detection and quantification of a target nucleic acid in switch-on mode; (3) detection and quantification of a target molecule in switch-on mode; (4) detection and quantification of target BER enzyme activity in switch-on mode; and (5) detection and quantification of a target nuclease in switch-on mode.

DISCLOSURE OF INVENTION

Technical Problem

It is a main object of the present invention to provide a method of detecting and quantifying a target nucleic acid using a DNA aptamer comprising a single-stranded DNA that specifically recognizes the target nucleic acid.

Another object of the present invention is to provide a method of detecting and quantifying a target nucleic acid using an aptamer comprising a single-stranded DNA complementary to a blocker nucleic acid having a sequence complementary to the target nucleic acid.

Still another object of the present invention is to provide a method of detecting and quantifying a target molecule using an aptamer comprising a single-stranded DNA complementary to a blocker DNA that specifically recognizes the target molecule and that has a sequence binding to the target molecule.

A further another object of the present invention is to provide a method of detecting and quantifying target BER (Base Excision Repair) enzyme activity using an aptamer comprising a single-stranded DNA complementary to a blocker nucleic acid having a nucleotide sequence specific for the target BER (Base Excision Repair) enzyme.

A further object of the present invention is to provide a method of detecting and quantifying target nuclease activity using an aptamer comprising a single-stranded DNA complementary to a blocker nucleic acid having a nucleotide sequence specific for the target nuclease.

Technical Solution

To achieve the above object, the present invention provides a method of detecting or quantifying a target nucleic acid in switch-off mode using nucleic acid polymerase activity controlled by the target nucleic acid comprises: (a) adding a nucleic acid polymerase to a mixture containing an aptamer comprising a single-stranded nucleic acid, which specifically recognizes the target nucleic acid, and a detection sample which is supposed to contain the target nucleic acid, and reacting the nucleic acid polymerase with the mixture to thereby bind the nucleic acid polymerase to an aptamer-target nucleic acid complex; (b) mixing a mixture containing a primer and a signal-generating substance with the reaction product of step (a), followed by a primer extension reaction; and (c) analyzing the primer extension reaction of step (b) to thereby detect or quantify the target nucleic acid.

The provides also provides a method of detecting or quantifying a target nucleic acid in switch-on mode using nucleic acid polymerase activity controlled by the target nucleic acid comprises: (a) adding a nucleic acid polymerase and a detection sample, which is presumed to contain the target nucleic acid, to a mixture containing a blocker nucleic acid, which has a nucleotide sequence complementary to the target nucleic acid, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the target nucleic acid.

The provides also provides a method of detecting or quantifying a target molecule in switch-on mode using nucleic acid polymerase activity controlled by the target nucleic acid comprises: (a) adding a nucleic acid polymerase and a detection sample, which is presumed to contain the target molecule, to a mixture containing a blocker nucleic acid having a nucleotide sequence, which specifically recognizes and binds to the target molecule, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the target molecule.

The provides also provides a method of detecting or quantifying target BER (Base Excision Repair) enzyme activity in switch-on mode using nucleic acid polymerase activity controlled by BER (Base Excision Repair) enzyme comprises: (a) adding a nucleic acid polymerase and a detection sample, which is presumed to contain the target BER enzyme, to a mixture containing a blocker nucleic acid, which has a nucleotide sequence specific for the target BER enzyme, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the activity of the target BER (Base Excision Repair) enzyme.

The provides also provides a method of detecting or quantifying target nuclease activity in switch-on mode using nucleic acid polymerase activity controlled by target nuclease comprises:

(a) adding a nucleic acid polymerase and a detection sample, which is presumed to contain the target nuclease, to a mixture containing a blocker nucleic acid, which has a nucleotide sequence specific for the target nuclease, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance to the reaction product of step (a), followed by a primer extension reaction; and (c) analyzing the primer extension reaction of step (b) to thereby detect or quantify the target nuclease activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a schematic view showing target DNA-induced switching of DNA polymerase activity and a principle by which the switching is analyzed using a TaqMan probe. Specifically, FIG. 1 is a schematic view showing a principle by which a target nucleic acid is detected and quantified based on a DNA aptamer that binds specifically to Taq DNA polymerase to inhibit the activity of the enzyme.

FIG. 2 shows the results of testing the feasibility of target DNA-induced switching of DNA polymerase activity. Specifically, FIG. 2 shows experimental results indicating that DNA aptamers designed so as to contain various single-stranded nucleotide sequences inhibit polymerase activity by binding to complementary target nucleic acids. (a) The change in fluorescence intensity of a TaqMan probe during a primer extension reaction. (b) The change in a fluorescence signal after 200 minutes of a primer extension reaction. Herein, $F_{200}$ and $F_0$ stand for the fluorescence intensities of the TaqMan probe after 200 minutes and 0 minute of the primer extension reaction, respectively. NC: polymerase-free sample, PC: polymerase-containing sample, (1): a sample obtained by adding an original DNA aptamer, which is a positive control, to PC, (#, a): samples obtained by adding only an aptamer to PC without a target nucleic acid, and (#, p): samples obtained by adding a target nucleic acid and an aptamer to PC. The final concentrations of the polymerase, DNA aptamer and target nucleic acid used in this experiment are 5.5 nM, 100 nM and 100 nM, respectively.

FIG. 3 shows experimental results obtained by applying the control of polymerase activity by target nucleic acid, shown in FIG. 2, for the detection and quantification of urea (*Ureaplasma urealyticum*), a pathogen that causes sexually transmitted disease. (a) The change in fluorescence intensity of a TaqMan probe during a primer extension reaction. (b) The change in a fluorescence signal after 50 minutes of a primer extension reaction. Herein, $F_{50}$ and $F_0$ stand for the fluorescence intensities of the TaqMan probe after 50 minutes and 0 minute of the primer extension reaction, respectively. (c) PAGE(Polyacrylamide gel electrophoresis) image, NC: polymerase-free sample, PC: polymerase-containing sample, (1): a sample obtained by adding only a urea-specific aptamer to PC without a complementary urea target nucleic acid, (2): a sample obtained by adding a complementary urea target nucleic acid and a urea-specific aptamer to PC, and (3): a sample obtained by adding a non-complementary chlamydia target nucleic acid and a urea-specific aptamer to PC. The final concentrations of the polymerase, DNA aptamer and target nucleic acid used in this experiment are 5.5 nM, 200 nM and 100 nM, respectively.

FIG. 4 shows the results of measuring the sensitivity of the system of the present invention for the detection and quantification of urea target DNA. Specifically, FIG. 4 shows the results of measuring fluorescence signals occurring when varying concentrations of urea DNA were added based on optimal conditions determined by the experiment. (a) The change in fluorescence intensity of a TaqMan probe during a primer extension reaction. In the presence of varying concentrations of urea target DNA, a urea-specific aptamer was added to a polymerase-containing sample. (b) The change in a fluorescence signal after 50 minutes of a primer extension reaction in the presence of varying concentrations of urea target DNA. Herein, $F_{50}$ and $F_0$ stand for the fluorescence intensities of the TaqMan probe after 50 minutes and 0 minute of the primer extension reaction, respectively. Inset in (b): a linear graph showing the change in fluorescence intensity after 50 minutes of a primer extension reaction at urea target DNA concentration (0-10 nM). The final concentrations of the polymerase and DNA aptamer used in this experiment are 5.5 nM and 200 nM, respectively.

FIG. 5 shows the results of measuring the sensitivity of the system of the present invention for the detection and quantification of Chlamydia target DNA. Specifically, FIG. 5 shows the results indicating that the newly developed system for detection and quantification of target DNA can be universally used for detection and quantification of various target DNAs. (a) The change in fluorescence intensity of a TaqMan probe during a primer extension reaction. In the presence of varying concentrations of chlamydia target DNA, a chlamydia-specific aptamer was added to a polymerase-containing sample. (b) The change in a fluorescence signal after 50 minutes of a primer extension reaction in the presence of varying concentrations of chlamydia target DNA. Herein, $F_{50}$ and $F_0$ stand for the fluorescence intensities of the TaqMan probe after 50 minutes and 0 minute of the primer extension reaction, respectively. Inset in (b): a linear graph showing the change in fluorescence intensity after 50 minutes of a primer extension reaction at chlamydia target DNA concentration (0-10 nM). The final concentrations of the polymerase and DNA aptamer used in this experiment are 5.5 nM and 200 nM, respectively.

FIG. 6 is a schematic view showing target DNA-induced switching of polymerase activity and a principle by which the switching is analyzed using a TaqMan probe. Specifically, FIG. 6 is a schematic view showing a principle by which target DNA is detected and quantified by introduction of blocker DNA, in order to embody an invention that operates in switch-on mode (signal-on mode) in addition to the switch-off mode (signal-off mode) embodied as described above.

FIG. 7 shows the results of detecting and quantifying urea target DNA using a switching-on system. Specifically, FIG. 7 shows experimental results for the control of polymerase activity by target DNA in a target DNA detection and quantification system designed to operate in switch-on mode (signal-on mode). (a) Varying concentrations of urea-specific blocker DNA were added to samples containing polymerase and DNA aptamer. (b) Free DNA aptamer (1), or DNA aptamer in the presence of urea-specific blocker DNA (2), or DNA aptamer in the presence of urea-specific blocker DNA supplied with complementary urea target DNA (3), or DNA aptamer in the presence of urea-specific blocker DNA supplied with non-complementary chlamydia target DNA (4) was added to samples containing DNA polymerase. (c) The changes in fluorescence intensities of the TaqMan probe during primer extension reactions. Varying concentrations of urea target DNAs were added to samples containing DNA polymerase and a DNA aptamer bound to urea-specific blocker DNA. (d) The change in a fluorescence signal after 50 minutes of a primer extension reaction in the presence of varying concentrations of urea target DNA. Inset in (d): a linear graph showing the change in fluorescence intensity after 50 minutes of a primer extension reaction at urea target DNA concentration (0-20 nM). The final concentrations of the polymerase, DNA aptamer, and the urea-specific blocker DNA used in this experiment are 5.5 Nm, 200 nM, and 20 nM, respectively.

FIG. 8 is a schematic view showing target molecule-induced switching of DNA polymerase activity and a principle by which the switching is analyzed using a TaqMan probe.

FIG. 9 is a schematic view showing UDG target enzyme-induced switching of DNA polymerase activity and a principle by which the switching is analyzed using a TaqMan probe.

FIG. 10 shows the results of testing the feasibility of UDG target enzyme-induced switching of DNA polymerase activity. Specifically, FIG. 10 shows the results of testing the effect of UDG on DNA polymerase activity using a DNA aptamer designed so as to respond specifically to UDG. (a) The change in fluorescence intensity of a TaqMan probe during a primer extension reaction. (b) The change in a fluorescence signal after 50 minutes of a primer extension reaction. Herein, $F_{50}$ and $F_0$ stand for the fluorescence intensities of the TaqMan probe after 50 minutes and 0 minute of the primer extension reaction, respectively. DNA polymerase was added to samples containing UDG aptamer (1), or UDG aptamer in the presence of UDG blocker (2), or UDG aptamer in the presence of UDG blocker supplied with UDG (3), or UDG aptamer in the presence of control UDG blocker (4), or UDG aptamer in the presence of control UDG blocker supplied with UDG (5). The final concentrations of the polymerase, UDG aptamer, UDG blocker, and UDG used in this experiment are 5.5 nM, 200 nM, 10 nM, and 0.5 U/mL, respectively.

FIG. 11 shows the results of measuring the sensitivity of the system of the present invention for the detection and quantification of UDG target enzyme. Specifically, FIG. 11 shows the results of measuring fluorescence signals occurring when varying concentrations of UDG were added based on the optimal conditions determined by the above-described experiment. (a) The change in fluorescence intensity of a TaqMan probe during a primer extension reaction. Varying concentrations of UDG were added to UDG detection probe samples comprising an UDG aptamer and an UDG blocker. (b) The change in a fluorescence signal after 50 minutes of a primer extension reaction in the presence of varying concentrations of UDG. Herein, $F_{50}$ and $F_0$ stand for the fluorescence intensities of the TaqMan probe after 50 minutes and 0 minute of the primer extension reaction, respectively. Inset in (b): a linear graph showing the change in fluorescence intensity after 50 minutes of a primer extension reaction at UDG concentration (0-0.3 U/mL). The final concentrations of the polymerase, UDG aptamer and UDG blocker used in this experiment are 5.5 Nm, 200 nM, 10 nM, and 10 nM, respectively.

FIG. 12 shows the results of testing the specificity of the system of the present invention for the detection and quantification of UDG target enzyme. The change in a fluorescence signal after 50 minutes of a primer extension reaction. Herein, $F_{50}$ and $F_0$ stand for the fluorescence intensities of the TaqMan probe after 50 minutes and 0 minute of the primer extension reaction, respectively. DNA polymerase was added to samples comprising Blank (1), UDG (2), hAAG (3), hOGG1 (4), Fpg (5), BamHI (6), Exo I (7), and Lambda exonuclease (8). The final concentrations of the polymerase, UDG aptamer, UDG blocker, UDG and another enzyme used in this experiment are 5.5 nM, 200 nM, 10 nM, 0.5 U/mL and 5 U/mL, respectively.

BEST MODE FOR CARRYING OUT THE INVENTION

In the present invention, a highly sensitive, enzyme-based detection and quantification system, which does not need to be labeled with an inhibitor and can be universally used for detection and quantification of various target DNAs, has been developed. In the present invention, Taq DNA polymerase, which performs a DNA extension reaction, and a DNA aptamer which binds specifically to the Taq DNA polymerase to inhibit the DNA polymerase activity, were introduced (Dang et al., *Journal of Molecular Biology*, 264:268-278, 1996; Lin et al., *Journal of Molecular Biology*, 271:100-111, 1997; Yakimovich et al., *Biochemistry-Moscow*, 68:228-235, 2003). Specifically, a DNA aptamer for detection and quantification of target nucleic acid was designed so as to comprise a single-stranded DNA that specifically recognizes the target nucleic acid, and it could be seen that, only when the single-stranded DNA was stabilized by binding to the target nucleic acid, it could bind to the Taq DNA polymerase to inhibit the DNA polymerase activity.

Furthermore, a DNA aptamer system which inhibits polymerase activity by binding to blocker DNA has also been developed. Because the blocker DNA was designed so as to have a sequence complementary to target nucleic acid, the presence of the target nucleic acid separates the blocker DNA from the DNA aptamer. As a result, the DNA aptamer no longer inhibits polymerase activity, and thus the characteristic activity of the polymerase is restored.

This change in polymerase activity by the interaction between the target nucleic acid and the DNA aptamer could be analyzed by real-time measurement of a fluorescence signal occurring during a primer extension reaction based on a TaqMan probe. The present invention has an advantage over a conventional nucleic acid-based detection technology (Hutter et al., *Trends in Pharmacological Sciences*, 34:497-507, 2013) in that various target nucleic acids can be analyzed based on a change in the single-stranded nucleotide sequence of the DNA aptamer which is a portion that recognizes the target nucleic acid, while a signal detection portion is maintained without changes, because the portion that recognizes the target nucleic acid and the signal detection portion are separated from each other. Furthermore, the present invention has the capability to detect and quantify various biomolecules and chemical substances in addition to target nucleic acids with high sensitivity by using an aptamer sequence, which specifically recognizes cells, proteins, small-molecular substances, etc., as a blocker DNA. The TaqMan probe-based signal generation technology used in the present invention may be easily replaced with color development and electrochemical technologies, etc.

In the present invention, it has been found that, only when a DNA aptamer that specifically recognizes Taq DNA polymerase to inhibit the polymerase activity is modified so that it will form a stable structure by binding to target nucleic acid, it can inhibit the polymerase activity. Based on this finding, a new method that can be universally used for the detection and quantification of various target nucleic acids could be developed.

The attempted polymerase activity control induced by target nucleic acid and the development of a detection and quantification system based thereon have not yet been reported, and the system of the present invention has advantages over a conventional nucleic acid-based detection technology in that it can detect and quantify various target nucleic acids based on a change in only the single-stranded nucleotide sequence of the DNA aptamer and in that the detection and quantification can be performed in a simple manner without labeling enzyme with an inhibitor. Furthermore, the present invention may be used for the detection and quantification of not only target nucleic acids, based on target-controlled polymerase activity, but also other biomolecules and chemical substances.

As used herein, the term "nucleic acid" means single-stranded or double-stranded DNA, RNA, and any chemical modifications thereof, and such modifications include, but are not limited to, backbone modifications, methylations, unusual base-pairing combinations, substitution of 5-bromouracil, and the like, provided only that the modifications do not interfere with amplification of selected nucleic acids.

As used herein, the term "aptamer" refers to a small single-stranded oligonucleotide that can specifically recognize its target molecule with high affinity. The aptamer in the present invention may have a length generally between about 15 and about 200 nucleotides, but not limited thereto. For example, the length of the aptamer may be below about 100 nucleotides, and preferably below about 80 nucleotides. The length of the aptamer that can be used in the present invention is not particularly limited, but may be about 96 nucleotides, and may be modified to have a length of 20-30 nucleotides through a post-SELEX process. If the total number of nucleotides is small, chemical synthesis and mass production are improved, and cost effectiveness increases. Further, easier chemical modification, higher stability and lower toxicity for application on a living body are provided.

The aptamer of the present invention can be chemically synthesis by the disclosure of the specification and a method known per se in the art. The aptamer may generally be prepared using the SELEX method or an improved version thereof [e.g., Ellington et al., *Nature*, 346:818-822, 1990; Tuerk et al., *Science*, 249:505-510, 1990]. The SELEX method refers to a method of identifying a DNA sequence specific for each molecule by selecting and amplifying a DNA or RNA having a high affinity for a particular molecular from a group of randomly synthesized DNAs or RNAs (J. W. Park et al., *Chemical Communications*, 48(15):2071-2073, 2012). In the SELEX method, an aptamer having a stronger binding affinity for the target molecule is concentrated and selected by increasing the number of rounds or using a competing substance. Hence, by adjusting the number of rounds of SELEX and/or changing the competitive condition, aptamers with different having different binding affinities, aptamers having different binding modes, or aptamers having the same binding affinity or binding mode but different nucleotide sequences can be obtained in some cases.

Each of the nucleotides contained in the aptamer of the present invention, which are the same or different, can be a nucleotide (i.e., an unsubstituted nucleotide) comprising a hydroxyl group at the 2' position of ribose (i.e., a ribose of a pyrimidine nucleotide) or a nucleotide having a hydroxyl group substituted by any atom or group at the 2' position of ribose. Examples of such nucleotides substituted by any atom or group include a nucleotide substituted by a hydrogen atom, a fluorine atom or an —O-alkyl group (e.g., —O-Me group), an —O-acyl group (e.g., —O—CHO group), or an amino group (e.g., —NH$_2$ group). The aptamer of the present invention may also be the nucleotide wherein at least one (e.g., 1, 2, 3 or 4) nucleotide comprises a hydroxyl group, or the above-described any atom or group, for example, at least two (e.g., 2, 3 or 4) groups selected from the group consisting of a hydrogen atom, a fluorine atom, a hydroxyl group and a methoxy group, at the 2' position of ribose. The aptamer of the present invention may also be one wherein all nucleotides identically comprise a hydroxyl group, or any atom or group mentioned above, for example, the identical group selected from the group consisting of a hydrogen atom, a fluorine atom, a hydroxyl group and an —O-Me group, at the 2' position of ribose.

The aptamer of the present invention may be one wherein a sugar residue (e.g., ribose or deoxyribose) of each nucleotide has been modified to increase the affinity of the aptamer for a target molecule or a target nucleic acid, the stability of the aptamer, and the like. As examples of the site to be modified in a sugar residue, one having the oxygen atom at the 2'-position, 3'-position and/or 4'-position of the sugar residue replaced with another atom, and the like can be mentioned. As examples of the modification, fluoration, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see e.g., Sproat et al., *Nucle. Acid. Res.* 19:733-738, 1991; Cotton et al., *Nucl. Acid. Res.* 19:2629-2635, 1991; Hobbs et al., *Biochemistry,* 12:5138-5145, 1973).

The aptamer of the present invention may also have a nucleic acid base (e.g., purine or pyrimidine) altered (e.g., chemical substitution) to increase its affinity for a target molecule or a target nucleic acid. Examples of such alterations include pyrimidine alteration at 5-position, purine alteration at 6- and/or 8-position(s), alteration with an extra-cyclic amine, substitution with 4-thiouridine, and substitution with 5-bromo or 5-iodo-uracil.

Also, the phosphate group contained in the aptamer of the present invention may be altered to confer resistance to nuclease and hydrolysis. For example, the P(O)O group may be replaced with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—), wherein each unit of R or R' is independently H or a substituted or unsubstituted alkyl (e.g., methyl, ethyl). The linking group is, for example, —O—, —N— or —S—, and nucleotides can bind to an adjoining nucleotide via these linking groups.

The alterations in the present invention may also include alterations such as capping at 3' and 5'. An alteration can further be performed by adding to an end a polyethylenegylcol, amino acid, peptide, inverted dT, nucleic acid, nucleosides, myristoyl, lithocolic-oleyl, docosanyl, lauroyl, stearoyl, palmitoyl, oleoyl, linoleoyl, other lipids, steroids, cholesterol, caffeine, vitamins, pigments, fluorescent substances, anticancer agent, toxin, enzymes, radioactive substance, biotin and the like (see U.S. Pat. Nos. 5,660,985 and 5,756,703).

An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible.

Regarding modifications of the 2'-position of ribose, the functional group at the 2'-position of ribose infrequently interacts directly with the target molecule, but in many cases, it is of no relevance, and can be substituted by another modified molecule. Hence, an aptamer often retains the activity thereof, unless the functional group involved in the direct binding to the target molecule is substituted or deleted.

In an example of the present invention, as a method for detection and quantification of target DNA in switch-off mode, an experiment was performed to confirm that DNA aptamers designed so as to comprise various single-stranded nucleotide sequences binds to complementary target nucleic acids to inhibit polymerase activity. As shown in FIGS. 2(a) and 2(b), it could be seen that, only in the presence of target nucleic acid complementary to the single-stranded nucleotide sequence of the DNA aptamer, the DNA aptamer inhibited polymerase activity, and thus a low fluorescence signal appeared. Furthermore, it could be seen that the extent to which the DNA aptamer inhibited polymerase activity in the presence of target nucleic acid was similar to the extent to which the original 78-mer DNA aptamer inhibited polymerase activity.

In another example of the present invention, an experiment was performed in which target nucleic acid-induced polymerase activity was used for the detection and quantification of urea (*Ureaplasma urealyticum*), a pathogen that causes sexually transmitted disease. As shown in FIGS. 3(a), 3(b) and 3(c), it could be seen that a DNA aptamer designed so as to bind specifically to urea DNA inhibited polymerase activity, only in the presence of urea DNA that is target nucleic acid. However, when the negative control Chlamydia (*Chlamydia trachomatis*) DNA that does not interact with a DNA aptamer was added, it could be seen that DNA polymerase activity was not inhibited and inherent high polymerase activity appeared.

In still another example of the present invention, an experiment was performed to measure fluorescence signals occurring when urea DNA were added at varying concentrations based on optimized conditions. As a result, it could be seen that, as the concentration of urea DNA increased, polymerase activity was inhibited, and thus reduced fluorescence signals occurred. Furthermore, it could be seen that the fluorescence signal decreased linearly in the urea DNA concentration range of 0 to 10 nM and that the detection limit was 0.91 nM.

In still another example of the present invention, an experiment was performed in which a method for detecting and quantifying target DNA in switch-off mode was universally used for the detection and quantification of various target nucleic acids. Thus, in this experiment, a DNA aptamer comprising a single-stranded DNA that binds specifically to Chlamydia DNA was designed and incubated with varying concentrations of Chlamydia DNA. As can be seen in FIG. 5, as the concentration of Chlamydia DNA increased, polymerase activity was inhibited, and as a result, reduced fluorescence signals occurred. It could be seen that the fluorescence signal decreased linearly in the Chlamydia DNA concentration range of 0 to 10 nM and that the detection limit was 1.47 nM.

The aptamers used in the present invention are as follows (underlines: conserved regions (SEQ ID NO: 21)):

```
Original DNA aptamer:
                                    (SEQ ID NO: 1)
5'-TTCT CGGT TGGT CTCT GGCG GAGC AAGA CCAG ACAA
TGTA CAGT ATTG GCCT GATC TTGT GTAT GATT CGCT TTTC
CC-3'

T20-aptamer:
                                    (SEQ ID NO: 2)
5'-TTTT TTTT TTTT TTTT TTTT CAAT GTAC AGTA TTG-3'

Random 1-aptamer:
                                    (SEQ ID NO: 4)
5'-AGTC AGTC AGTC AGTC AGTC CAAT GTAC AGTA TTG-3'

Random 2-aptamer:
                                    (SEQ ID NO: 6)
5'-ACTG ACTG ACTG ACTG ACTG CAAT GTAC AGTA TTG-3'

T20-aptamer(Reverse):
                                    (SEQ ID NO: 8)
5'-CAAT GTAC AGTA TTGT TTTT TTTT TTTT TTTT TTT-3'

Urea-specific aptamer 1:
                                    (SEQ ID NO: 9)
5'-TAGG ACGG TCAC CAGT ATTT TTAA TCAA TGTA CAGT
ATTG-3'

Chlamydia-specific aptamer:
                                    (SEQ ID NO: 12)
5'-TACA AGCT GCAA TCCC TTTT AAGA TCAA TGTA
CAGT ATTG-3'

Urea-specific aptamer 2:
                                    (SEQ ID NO: 14)
5'-A AAT ACTG GTGA CCGT CCTA CAAT GTAC AGTA TTG-
3'

UDG aptamer:
                                    (SEQ ID NO: 18)
5'-TTTT AA TTTT AA TTTT CAA TGT ACA GTA TTG-3'
```

Therefore, in a first aspect, the present invention is directed to a method of detecting or quantifying a target nucleic acid in switch-off mode using nucleic acid polymerase activity controlled by the target nucleic acid comprises: (a) adding a nucleic acid polymerase to a mixture containing an aptamer comprising a single-stranded nucleic acid, which specifically recognizes the target nucleic acid, and a detection sample which is supposed to contain the target nucleic acid, and reacting the nucleic acid polymerase with the mixture to thereby bind the nucleic acid polymerase to an aptamer-target nucleic acid complex; (b) mixing a mixture containing a primer and a signal-generating substance with the reaction product of step (a), followed by a primer extension reaction; and (c) analyzing the primer extension reaction of step (b) to thereby detect or quantify the target nucleic acid.

In the present invention, the single strand of the aptamer may have a nucleotide sequence complementary to the target nucleic acid. Furthermore, the aptamer may form a stable structure upon its binding to the target nucleic acid, and then bind to the nucleic acid polymerase to reduce the activity of the polymerase. In addition, the aptamer may have a conserved region represented by SEQ ID NO: 21 at its 5' terminus or 3' terminus. In addition, the aptamer may have a nucleotide sequence selected from the group consisting of SEQ ID NO: 1, SEQ ID NO: 2, SEQ ID NO: 4, SEQ ID NO: 6, SEQ ID NO: 8, SEQ ID NO: 9, and SEQ ID NO: 12.

In the present invention, the target nucleic acid may be selected from the group consisting of A20-target, random 1-target, random 2-target, complementary urea-target 1, non-complementary chlamydia-target 1, and complementary chlamydia-target 2, and the nucleic acid polymerase may be Taq DNA polymerase.

In the present invention, the mixture of step (a) may be heated at about 90° C. for about 5 minutes, and then cooled slowly to about 25° C., after which the nucleic acid polymerase may be added thereto and reacted. More specifically, the mixture of step (a) is heated at 90° C. for 5 minutes, and then cooled slowly to 25° C. at a rate of 0.1° C./sec, and incubated at 25° C. for 30 minutes, after which the nucleic acid polymerase is added thereto and reacted for 20 minutes to thereby bind the nucleic acid polymerase to the aptamer-target nucleic acid complex.

In the present invention, the mixture containing the signal-generating substance may further contain a template nucleic acid and a TaqMan probe.

In the present invention, the mixture containing the signal-generating substance, used in step (b), may be heated at about 90° for about 5 minutes, and then cooled slowly to about 25° C., after which it is subjected to a reaction that binds the primer and a TaqMan probe to a template nucleic acid, and then mixed with the reaction product of step (a). More specifically, the mixture containing the signal-generating substance, used in step (b), is heated at 90° C. for 5 minutes, and then cooled slowly to 25° C. at a rate of 0.1° C./sec, after which it is subjected to a reaction, which binds the primer and a TaqMan probe to a template nucleic acid, and then subjected to a reaction that binds the primer and a TaqMan probe to a template nucleic acid, for 60 minutes, and then mixed with the reaction product of step (a).

In the present invention, step (c) may comprise detecting or quantifying a signal derived from the primer extension reaction of step (b) to thereby determine the presence or absence of the target nucleic acid. Furthermore, the primer extension reaction may be performed at a temperature of 20 to 30° C., and the signal-generating substance may be labeled with a substance selected from the group consisting of radioisotopes, fluorescent substances, dyes, nanoparticles, enzymes, enzymatic substrates, luminescent substances, and substances containing an electrochemical functional group.

As shown in FIG. 1, the method of detecting or quantifying the target nucleic acid in switch-off mode using target nucleic acid-controlled nucleic acid polymerase activity according to the present invention is a method of detecting and quantifying the target nucleic acid using a characteristic in that the aptamer comprising the single-stranded nucleic acid forms a stable structure upon binding to the target nucleic acid, and then binds to the nucleic acid polymerase to reduce the activity of the polymerase.

As used herein, the term "sample" refers to a composition that contains or is presumed to contain target nucleic acid or target molecule and will be analyzed. The sample may be a sample collected from any one or more of, but not limited to, liquid, soil, air, food, waste, animal intestines, and animal tissues. Herein, examples of the liquid may be serum, blood, urine, water, tears, sweat, saliva, blood, serum, plasma, sputum, lymph, and cerebrospinal fluid. Examples of the water include river water, seawater, lake water, and rain water. Examples of the waste include sewage, waste water, and the like. The animals include the human body. Further, examples of the animal and plant tissues include mucous membranes, skin, cortices, hair, scales, eyes, tongues, cheeks, hooves, beaks, snouts, feet, hands, mouths, nipples, ears, noses, etc.

In another example of the present invention, in a target nucleic acid detection and quantification system designed so as to operate a method of detecting and quantifying target DNA in switch-on mode, an experiment for target nucleic acid-controlled polymerase activity was performed (FIG. 7). Specifically, blocker DNA that specifically recognizes urea DNA was designed, and a DNA aptamer suitable for the blocker DNA was constructed to perform an experiment. It could be seen that, as the concentration of the blocker DNA increased, polymerase activity was inhibited. Using a blocker DNA concentration of 20 nM determined to be optimal in the experiment, urea DNA detection and quantification was performed. As shown in FIG. 7(b), it could be seen that, only when the target nucleic acid urea DNA was present (3), polymerase was activated, and a high fluorescence signal occurred. However, when the negative control Chlamydia DNA was present (4), polymerase activity continued to be inhibited, and a low fluorescence signal occurred. Fluorescence signals occurring when varying concentrations of urea DNA were added under the conditions selected through the experiment were measured. As can be seen in FIGS. 7(c) and 7(d), as the concentration of urea DNA increased, polymerase activity increased, and thus high fluorescence signals occurred. Furthermore, it could be seen that the fluorescence signal increased linearly in the urea DNA concentration range of 0 to 20 nM and that the detection limit was 2.67 nM.

Therefore, in a second aspect, the present invention is directed to a method of detecting or quantifying a target nucleic acid in switch-on mode using nucleic acid polymerase activity controlled by the target nucleic acid comprises: (a) adding a nucleic acid polymerase and a detection sample, which is presumed to contain the target nucleic acid, to a mixture containing a blocker nucleic acid, which has a nucleotide sequence complementary to the target nucleic acid, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the target nucleic acid.

In the present invention, the single strand of the aptamer may have a nucleotide sequence complementary to the blocker nucleic acid, and the aptamer may form a stable structure upon its binding to the blocker nucleic acid, and then bind to the nucleic acid polymerase to reduce the activity of the polymerase. Furthermore, the aptamer may have a conserved region represented by SEQ ID NO: 21 at its 5' terminus or 3' terminus, and the aptamer may have a nucleotide sequence represented by SEQ ID NO: 14.

In the present invention, the target nucleic acid may be either complementary urea-target 2 or non-complementary chlamydia-target 2, and the nucleic acid polymerase may be Taq DNA polymerase. The primer extension reaction may be performed at a temperature of 20 to 30° C.

In the present invention, the mixture of step (a) may be heated at about 90° C. for about 5 minutes, and then cooled slowly to about 25° C., after which the nucleic acid polymerase may be added thereto and reacted. More specifically, the mixture of step (a) is heated at 90° C. for 5 minutes, and then cooled slowly to 25° C. at a rate of 0.1° C./sec, and incubated at 25° C. for 30 minutes, after which the nucleic acid polymerase is added thereto and reacted for 20 minutes to thereby bind the nucleic acid polymerase to the aptamer-blocker nucleic complex.

In the present invention, the mixture containing the signal-generating substance may further contain a template nucleic acid and a TaqMan probe.

In the present invention, the mixture containing the signal-generating substance, used in step (b), may be heated at about 90° for about 5 minutes, and then cooled slowly to about 25° C., after which it is subjected to a reaction that binds the primer and a TaqMan probe to a template nucleic acid, and then mixed with the reaction product of step (a). More specifically, the mixture containing the signal-generating substance, used in step (b), is heated at 90° C. for 5 minutes, and then cooled slowly to 25° C. at a rate of 0.1° C./sec, after which it is subjected to a reaction, which binds the primer and a TaqMan probe to a template nucleic acid, and then subjected to a reaction that binds the primer and a TaqMan probe to a template nucleic acid, for 60 minutes, and then mixed with the reaction product of step (a).

In the present invention, the signal-generating substance may be labeled with a substance selected from the group consisting of radioisotopes, fluorescent substances, dyes, nanoparticles, enzymes, enzymatic substrates, luminescent substances, and substances containing an electrochemical functional group, and step (c) may comprise detecting or quantifying a signal derived from the primer extension reaction of step (b) to thereby determine the presence or absence of the target nucleic acid.

In the present invention, the blocker nucleic acid may be either a blocker DNA or a blocker RNA, and the blocker nucleic acid may be a urea-specific blocker having a nucleotide sequence represented by SEQ ID NO: 15.

As shown in FIG. 6, the method of detecting or quantifying the target nucleic acid in switch-on mode using target nucleic acid-controlled nucleic acid polymerase activity according to the present invention is a method of detecting and quantifying the target nucleic acid using a characteristic in that the aptamer comprising the single-stranded nucleic acid forms a stable structure upon its binding to the blocker nucleic acid, and then binds to the nucleic acid polymerase to reduce the activity of the polymerase.

In another example of the present invention, in a method of detecting and quantifying UDG in switch-on mode, as results of testing the effect of UDG on polymerase activity using a DNA aptamer designed so as to respond specifically to UDG, as can be seen in FIGS. 10(a) and 10(b), only when UDG target enzyme was present, polymerase activity increased, and thus high fluorescence signals occurred (3). However, when an experiment was performed in which a DNA containing thymine in place of uracil nucleobase was introduced to a blocker DNA complementary to the single-stranded region of the DNA aptamer, it could be seen that polymerase activity was inhibited by the DNA aptamer regardless of the presence or absence of UDG (4 and 5). This suggests that the cleavage of uracil nucleobase by UDG plays an important role in the restoration of polymerase activity and that UDG enzyme activity can be detected and quantified based on the cleavage of uracil nucleobase by UDG.

In another example of the present invention, an experiment was performed which measures fluorescence signals occurring when UDG was added at varying concentrations based on the optimal conditions determined by the experiment (FIG. 11). As a result, it could be seen that, as the concentration of UDG increased, polymerase activity increased, and thus high fluorescence signals occurred. Furthermore, it could be seen that the fluorescence signal increased linearly in the UDG concentration region of 0 to 0.3 U/mL and that the detection limit was 0.024 U/mL.

In another example of the present invention, an experiment was performed which measures the specificity of the newly developed system for analyzing a target enzyme in the present invention (FIG. 12). It could be seen from the results in FIG. 12 that when hAAG (human alkyladenine DNA glycosylase) (3), hOGG1 (human 8-oxoguanine DNA glycosylase 1) (4), Fpg (formamidopyrimidine-DNA glycosylase) (5), BamHI (6), Exo I (7) or Lambda exonuclease (8) was present, the polymerase activity inhibited by the DNA aptamer was not restored, and a low fluorescence signal appeared. However, when the target enzyme UDG was present, the DNA aptamer was converted to a DNA aptamer structure containing a single strand by the cleavage of uracil nucleobase, and thus polymerase was activated and a high fluorescence signal appeared.

A "target molecule" that is used in the present may be any one selected from the group consisting of a nucleic acid, a carbohydrate, a lipid, a protein, a peptide, an aptamer, an antigen, an antibody, a hapten, a low-molecular-weight material, a macromolecular complex, a cell, a pharmaceutical agent, an organic compound, and an inorganic compound, but is not limited thereto. Herein, the term "low-molecular-weight material" is meant to include non-polar low-molecular-weight compounds such as bisphenol A.

Therefore, in a third aspect, the present invention is directed to a method of detecting or quantifying a target molecule in switch-on mode using nucleic acid polymerase activity controlled by the target nucleic acid comprises: (a) adding a nucleic acid polymerase and a detection sample, which is presumed to contain the target molecule, to a mixture containing a blocker nucleic acid having a nucleotide sequence, which specifically recognizes and binds to the target molecule, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the target molecule.

In the present invention, the single strand of the aptamer may have a nucleotide sequence complementary to the blocker nucleic acid, and the aptamer may form a stable structure upon its binding to the blocker nucleic acid, and then bind to the nucleic acid polymerase to reduce the activity of the polymerase. Furthermore, the aptamer may have a conserved region represented by SEQ ID NO: 21 at its 5' terminus or 3' terminus.

In the present invention, the blocker nucleic acid may be a DNA or RNA which specifically recognizes and binds to the target molecule. The target molecule may be any one selected from the group consisting of a nucleic acid, a carbohydrate, a lipid, a protein, a peptide, an aptamer, an antigen, an antibody, a hapten, a low-molecular-weight material, a macromolecular complex, a cell, a pharmaceutical agent, an organic compound, and an inorganic compound.

In the present invention, the nucleic acid polymerase may be Taq DNA polymerase, and the primer extension reaction may be performed at a temperature of 20 to 30° C. The signal-generating substance may be labeled with a substance selected from the group consisting of radioisotopes, fluorescent substances, dyes, nanoparticles, enzymes, enzymatic substrates, luminescent substances, and substances containing an electrochemical functional group, and step (c) may comprise detecting or quantifying a signal derived from the primer extension reaction of step (b) to thereby determine the presence or absence of the target nucleic acid. The mixture containing the signal-generating substance may further contain a template nucleic acid and a TaqMan probe.

As shown in FIG. 8, the method of detecting or quantifying the target molecule in switch-on mode using target molecule-controlled nucleic acid polymerase activity according to the present invention is a method of detecting and quantifying the target nucleic acid using a characteristic in that the aptamer comprising the single-stranded nucleic acid forms a stable structure upon its binding to the blocker nucleic acid, and then binds to the nucleic acid polymerase to reduce the activity of the polymerase.

In a fourth aspect, the present invention is directed to a method of detecting or quantifying target BER (Base Excision Repair) enzyme activity in switch-on mode using nucleic acid polymerase activity controlled by BER (Base Excision Repair) enzyme comprises: (a) adding a nucleic acid polymerase and a detection sample, which is presumed to contain the target BER enzyme, to a mixture containing a blocker nucleic acid, which has a nucleotide sequence specific for the target BER enzyme, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance with the reaction product of step (a), followed by a primer extension reaction; and (c) analyzing the primer extension reaction of step (b) to thereby detect or quantify the activity of the target BER (Base Excision Repair) enzyme.

In the present invention, the single strand of the aptamer may have a nucleotide sequence complementary to the blocker nucleic acid, and the aptamer may form a stable structure upon its binding to the blocker nucleic acid, and then bind to the nucleic acid polymerase to reduce the activity of the polymerase. Furthermore, the aptamer may have a conserved region represented by SEQ ID NO: 21 at its 5' terminus or 3' terminus. The aptamer may have a nucleotide sequence represented by SEQ ID NO: 18.

In the present invention, the blocker nucleic acid may be a DNA which is used as a substrate for the target BER enzyme. The blocker nucleic acid may be a UDG (uracil DNA glycosylase) blocker having a nucleotide sequence represented by SEQ ID NO: 19, which is used as a substrate for the target BER enzyme, and the target BER enzyme may be a UDG (uracil DNA glycosylase).

In the present invention, the nucleic acid polymerase may be Taq DNA polymerase, and the primer extension reaction may be performed at a temperature of 20 to 30° C.

In the present invention, the mixture of step (a) may be heated at about 90° C. for about 5 minutes, and then cooled slowly to about 37° C., after which the detection sample, which is presumed to contain the target BER (Base Excision Repair) enzyme, is added thereto and the resultant mixture is cooled slowly to about 25° C., after which a target nucleic acid polymerase may be added thereto and reacted. More specifically, the mixture of step (a) is heated at 90° C. for 5 minutes, and then cooled slowly to 37° C. at a rate of 0.1° C./sec, and incubated at 37° C. for 20 minutes, after which the detection sample, which is presumed to contain the target BER (Base Excision Repair) enzyme, is added thereto and then the resultant mixture is cooled slowly to 25° C. at a rate of 0.1° C./sec, and incubated at 25° C. for 5 minutes, after which the nucleic acid polymerase is added thereto and reacted at 25° C. for 20 minutes to thereby bind the nucleic acid polymerase to the aptamer-blocker nucleic acid complex.

In the present invention, the mixture containing the signal-generating substance may further contain a template nucleic acid and a TaqMan probe.

In the present invention, the mixture containing the signal-generating substance of step (b) may be heated at about 90° C. for about 5 minutes, and then cooled slowly to about 25° C., followed by a reaction that binds a primer and a TaqMan probe to the template and then is mixed with the reaction product of step (a). More specifically, the mixture containing the signal-generating substance of step (b) may be heated at 90° C. for 5 minutes, and then cooled slowly to 25° C. at a rate of 0.1° C./sec, followed by the reaction that binds the primer and the TaqMan probe to the template at 25° C. for 60 minutes and then is mixed with the reaction product of step (a).

In the present invention, the signal-generating substance may be labeled with a substance selected from the group consisting of radioisotopes, fluorescent substances, dyes, nanoparticles, enzymes, enzymatic substrates, luminescent substances, and substances containing an electrochemical functional group, and step (c) may comprise detecting or quantifying a signal derived from the primer extension reaction of step (b) to thereby analyze the activity of the target BER (Base Excision Repair) enzyme.

As shown in FIG. 9, the method of detecting or quantifying the BER (Base Excision Repair) enzyme in switch-on mode using target BER (Base Excision Repair) enzyme-controlled nucleic acid polymerase activity according to the present invention is a method of detecting and quantifying the target nucleic acid using a characteristic in that the aptamer comprising the single-stranded nucleic acid forms a stable structure upon its binding to the blocker nucleic acid, and then binds to the nucleic acid polymerase to reduce the activity of the target BER (Base Excision Repair) enzyme.

In a fifth aspect, the present invention is directed to a method of detecting or quantifying target nuclease activity in switch-on mode using nucleic acid polymerase activity controlled by target nuclease comprises: (a) adding a nucleic acid polymerase and a detection sample, which is presumed to contain the target nuclease, to a mixture containing a blocker nucleic acid, which has a nucleotide sequence specific for the target nuclease, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex; (b) mixing a mixture containing a primer and a signal-generating substance to the reaction product of step (a), followed by a primer extension reaction; and (c) analyzing the primer extension reaction of step (b) to thereby detect or quantify the target nuclease activity.

In the present invention, the single strand of the aptamer may have a nucleotide sequence complementary to the blocker nucleic acid, and the aptamer may form a stable structure upon its binding to the blocker nucleic acid, and then bind to the nucleic acid polymerase to reduce the activity of the polymerase. Furthermore, the aptamer may have a conserved region represented by SEQ ID NO: 21 at its 5' terminus or 3' terminus.

In the present invention, the blocker nucleic acid may be a DNA or RNA which is used as a substrate for the target nuclease. In the present invention, the nucleic acid polymerase may be Taq DNA polymerase, and the primer extension reaction may be performed at a temperature of 20 to 30° C.

In the present invention, the signal-generating substance may be labeled with a substance selected from the group consisting of radioisotopes, fluorescent substances, dyes, nanoparticles, enzymes, enzymatic substrates, luminescent substances, and substances containing an electrochemical functional group, and step (c) may comprise detecting or quantifying a signal derived from the primer extension reaction of step (b) to thereby analyze the activity of the target nucleic acid enzyme. The mixture containing the signal-generating substance may further contain a template nucleic acid and a TaqMan probe.

As shown in FIG. 9, the method of detecting or quantifying the target nucleic acid enzyme activity in switch-on mode using target nucleic acid enzyme-controlled nucleic acid polymerase activity according to the present invention is a method of detecting and quantifying the target nucleic acid using a characteristic in that the aptamer comprising the single-stranded nucleic acid forms a stable structure upon its binding to the blocker nucleic acid, and then binds to the nucleic acid polymerase to reduce the activity of the target nucleic acid enzyme.

FIG. 1 is a schematic view showing target nucleic acid-induced switching of nucleic acid polymerase activity and a principle by which the polymerase activity is analyzed using a TaqMan probe. More specifically, FIG. 1 is a schematic view showing a principle by which target nucleic acid is detected and quantified based on a DNA aptamer that binds specifically to Taq DNA polymerase to inhibit the activity of the polymerase. If the target nucleic acid to be detected and quantified is not present, the DNA aptamer designed so as to comprise a single-stranded DNA region will not recognize polymerase, and thus the polymerase will have inherent high activity.

However, if the target nucleic acid is present, it will bind specifically to the single-stranded DNA region of the DNA aptamer, and the DNA aptamer stabilized by the binding will bind to polymerase to inhibit the activity of the polymerase (1, Target recognition). The polymerase activity controlled by the target nucleic acid as described above can be analyzed through a primer extension reaction based on the TaqMan probe.

If the target nucleic acid is not present, cleavage of the TaqMan probe will be induced by the high activity of polymerase, and thus a high fluorescence signal will appear. However, if the target nucleic acid is present, the polymerase activity will be inhibited by the DNA aptamer, and thus the fluorescence signal arising from the TaqMan probe will be reduced. As described above, the target nucleic acid can be easily detected and quantified by observing structural stabilization of the DNA aptamer, caused by binding of the target nucleic acid, and inhibition of the polymerase activity and the change in the fluorescence signal generated, which are caused by the structural stabilization.

Furthermore, the present invention has an advantage in that various target nucleic acids can be analyzed in a cost-effective and easy manner by changing only the single-stranded nucleotide sequence of the DNA aptamer which is a portion that recognizes the target nucleic acid, while maintaining the signal detection portion without changes, because the portion that recognizes the target nucleic acid and the signal detection portion are separated from each other.

FIG. 6 is a schematic view showing a principle by which a target nucleic acid is detected and quantified through introduction of a blocker DNA, in order to embody an invention that operates in switch-on mode (signal-on mode) in addition to the switch-off mode (signal-off mode) embodied as described above. As shown in FIG. 6, if the target nucleic acid to be detected and quantified is not present, the DNA aptamer stabilized by the blocker DNA will inhibit polymerase activity, and thus a low fluorescence signal will appear. However, if the target nucleic acid is not present, the blocker DNA will be separated from the DNA aptamer so that the DNA aptamer will no longer inhibit the polymerase activity. As a result, the polymerase activity will increase, and a high fluorescence signal will appear.

FIG. 8 is a schematic view showing a principle by which a target molecule is detected and quantified according to the present invention. If the blocker DNA in the present invention is designed using an aptamer nucleotide sequence that can specifically recognize cells, proteins, small-molecular substances, etc., the presence of the target molecule will separate the blocker DNA from the DNA aptamer, and polymerase can produce a high fluorescence signal through its enzymatic activity. As a result, not only the target nucleic acid, but also a target cell, a target protein, a target small-molecular substance and the like, can be analyzed by controlling the nucleotide sequence of the blocker DNA in the system of the present invention.

FIG. 9 is a schematic view showing that the present invention can be used for analysis of target enzyme activity. Among various target enzymes, UDG (uracil DNA glycosylase) was selected as an example, and a complementary blocker DNA that binds to a single-stranded DNA contained in a DNA aptamer was designed so as to comprise uracil nucleobase.

Thus, only if the target enzyme (UDG) to be detected and quantified is present, cleavage of the uracil nucleobase will occur, and the blocker DNA containing (lacking) the uracil nucleobase will be separated from the single-stranded region of the DNA aptamer. The resulting unstabilized DNA aptamer will no longer inhibit polymerase, and thus the polymerase activity will increase. The increased polymerase activity is observed through a primer extension reaction based on the TaqMan probe.

The target enzyme-induced polymerase activity control attempted as described above and the detection and quantification system based thereon can advantageously be applied to a system for analyzing various target enzymes by changing only the single-stranded region of the DNA aptamer while maintaining a process of reading a TaqMan probe-based signal without changes.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Method of Detecting and Quantifying Target DNA in Switch-Off Mode

Reaction mixtures were separately prepared as part A and part B. Part A (total volume of 20 µL), composed of 1× Taq reaction buffer (10 mM Tris-HCl, pH 8.3, 50 mM KCl, 4 mM MgCl$_2$), 500 µM dNTPs, 400 nM DNA aptamer, and complementary target DNA at varying concentrations, was heated at 90° C. for 5 min, cooled slowly to 25° C. (0.1° C./sec) and incubated at 25° C. for 30 min. Taq DNA polymerase (11 nM) was then added to each solution and incubated for 20 min. Part B (total volume of 20 µL), composed of 1× Taq reaction buffer, 600 nM template, 600 nM primer, and 500 nM TaqMan probe, was heated at 90° C. for 5 min, cooled slowly to 25° C. (0.1° C. /sec) and incubated at 25° C. for 60 min. Part A and part B were mixed with each other, and the fluorescence signal was measured on a C1000™ thermal cycler (Bio-Rad, CA, USA). The fluorescence signal arising from TaqMan probe during the primer extension reaction was monitored at 2-min intervals at 25° C. The following Experimental Examples 1 to 4 were performed according to the method of Example 1.

Experimental Example 1

FIG. 2 shows experimental results indicating that DNA aptamers designed so as to contain various single-stranded nucleotide sequences inhibit polymerase activity by binding to complementary target nucleic acids. Table 1 below shows the DNA nucleotide sequences used in the experiment (underline: conserved region). As can be seen in FIGS. 2(a) and 2(b), only if the target nucleic acid complementary to the single-stranded nucleotide sequence of the DNA aptamer was present, the DNA aptamer inhibited polymerase activity, and thus low fluorescence signals appeared (2 to 5). In addition, it could be seen that the extent to which the DNA aptamer inhibited polymerase activity in the presence of target nucleic acid was similar to the extent to which the original 78-mer DNA aptamer inhibited polymerase activity.

TABLE 1

| Strand name | DNA sequence (5'→3') | SEQ ID NO |
| --- | --- | --- |
| Original DNA aptamer | TTCT CGGT TGGT CTCT GGCG GAGC AAGA CC AG <u>ACAA TGTA CAGT ATTG</u> GCCT GATC TTGT GTAT GATT CGCT TTTC CC | SEQ ID NO: 1 |

TABLE 1-continued

| Strand name | DNA sequence (5'→3') | SEQ ID NO |
|---|---|---|
| T20-aptamer | TTTT TTTT TTTT TTTT TTTT <u>CAAT GTAC AGTA TTG</u> | SEQ ID NO: 2 |
| A20-target | AAAA AAAA AAAA AAAA AAAA | SEQ ID NO: 3 |
| Random1-aptamer | AGTC AGTC AGTC AGTC AGTC <u>CAAT GTAC AGT A TTG</u> | SEQ ID NO: 4 |
| Random1-target | GACT GACT GACT GACT GACT | SEQ ID NO: 5 |
| Random2-aptamer | ACTG ACTG ACTG ACTG ACTG <u>CAAT GTAC AG TA TTG</u> | SEQ ID NO: 6 |
| Random2-target | CAGT CAGT CAGT CAGT CAGT | SEQ ID NO: 7 |
| T20-aptamer (Reverse) | CAAT GTAC AGTA TTGT TTTT TTTT TTTT TTTT TTT | SEQ ID NO: 8 |

Experimental Example 2

FIG. 3 shows experimental results obtained by applying the control of polymerase activity by target nucleic acid, shown in FIG. 2, for the detection and quantification of urea (*Ureaplasma urealyticum*), a pathogen that causes sexually transmitted disease. Table 2 below shows the DNA nucleotide sequences used in the experiment (underline: conserved region). As can be seen in FIGS. 3(a), 3(b) and 3(c), the DNA aptamer designed so as to bind specifically to urea DNA inhibited polymerase activity, only when urea DNA that is the target nucleic acid was present (2). However, it could be seen that, when the negative control Chlamydia (*Chlamydia trachomatis*) DNA that does not interact with the DNA aptamer was added, the DNA polymerase activity was not inhibited, and the inherent high activity appeared (3).

TABLE 2

| Strand name | DNA sequence (5'→3') | SEQ ID NO |
|---|---|---|
| Urea-specific aptamer 1 | TAGG ACGG TCAC CAGT ATTT TT AATC<u>AA TGTA CAGT ATTG</u> | SEQ ID NO: 9 |
| Complementary urea-target 1 | ATTA AAAA TACT GGTG ACCG TC CT A | SEQ ID NO: 10 |
| Non-complementary Chlamydia-target 1 | ATCT TAAA AGGG ATTG CAGC TT GT A | SEQ ID NO: 11 |

Experimental Example 3

FIG. 4 shows the results of measuring fluorescence signals occurring when varying concentrations of urea DNA were added based on optimal conditions determined by the experiment. It could be seen that, as the concentration of urea DNA increased, polymerase activity was inhibited, and thus reduced fluorescence signals occurred. Furthermore, it could be seen that the fluorescence signal decreased linearly in the urea DNA concentration range of 0 to 10 nM and that the detection limit was 0.91 nM. Table 2 above shows the DNA sequences used in the experiment.

Experimental Example 4

FIG. 5 shows the results indicating that the method of detecting and quantifying target DNA in switch-off mode can be universally used for the detection and quantification of various target nucleic acids. In this experiment, a DNA aptamer comprising a single-stranded DNA that binds specifically to Chlamydia DNA was designed and allowed to react with varying concentrations of Chlamydia DNA. Table 3 below shows the DNA sequence used in the experiment (underline: conserved region). As can be seen in FIG. 5, as the concentration of Chlamydia DNA increased, polymerase activity was inhibited, and thus reduced fluorescence signals occurred. Furthermore, it could be seen that the fluorescence signal decreased linearly in the Chlamydia DNA concentration range of 0 to 10 nM and that the detection limit was 1.47 nM.

TABLE 3

| Strand name | DNA sequence (5'→3') | SEQ ID NO |
|---|---|---|
| Chlamydia-specific aptamer | TACA AGCT GCAA TCCC TTTT AAGA T <u>CAA TGTA CAGT ATTG</u> | SEQ ID NO: 12 |

TABLE 3-continued

| Strand name | DNA sequence (5'→3') | SEQ ID NO |
|---|---|---|
| Complementary Chlamydia-target | ATCT TAAA AGGG ATTG CAGC TTGT A | SEQ ID NO: 13 |

Example 2

Method of Detecting and Quantifying Target DNA in Switch-On Mode

Reaction mixtures were separately prepared as part A and part B. Part A (total volume of 20 μL), composed of 1× Taq reaction buffer (10 mM Tris-HCl, pH 8.3, 50 mM KCl, 4 mM MgCl$_2$), 500 μM dNTPs, 400 nM DNA aptamer, 40 nM blocker DNA, and complementary target DNA at varying concentrations, was heated at 90° C. for 5 min, cooled slowly to 25° C. (0.1° C./sec) and incubated at 25° C. for 30 min. Taq DNA polymerase (11 nM) was then added to each solution and incubated for 20 min. Part B (total volume of 20 μL), composed of 1× Taq reaction buffer, 600 nM template, 600 nM primer, and 500 nM TaqMan probe, was heated at 90° C. for 5 min, cooled slowly to 25° C. (0.1 ° C. /sec) and incubated at 25° C. for 60 min. Part A and part B were mixed with each other, and the fluorescence signal was measured on a C1000™ thermal cycler (Bio-Rad, CA, USA). The fluorescence signal arising from TaqMan probe during the primer extension reaction was monitored at 2-min intervals at a polymerization reaction temperature of 20 to 30° C. (preferably 25° C.). The following Experimental Example 5 was performed according to the method of Example 2.

Experimental Example 5

FIG. 7 shows the results of detecting and quantifying urea target DNA using a switching-on system. Specifically, FIG. 7 shows experimental results for the control of polymerase activity by target DNA in a target DNA detection and quantification system designed so as to operate in switch-on mode (signal-on mode). In this experiment, a blocker DNA that specifically recognizes urea DNA was designed, and a DNA aptamer suitable for the blocker DNA was constructed to perform the experiment. Table 4 below shows the DNA sequences used in this experiment (underline: conserved region). FIG. 7(a) shows the results of optimizing the concentration of the introduced blocker DNA. It could be seen that, as the concentration of the blocker DNA increased, polymerase activity decreased. Using a blocker DNA concentration of 20 nM, determined to be optimal in the experiment, the detection and quantification of urea DNA was performed. As can be seen in FIG. 7(b), only when urea DNA that is the target nucleic acid was present (3), it could be seen that polymerase was activated, and a high fluorescence signal occurred. However, when Chlamydia DNA that is the negative control was present (4), it could be seen that polymerase activity continued to be inhibited, and a low fluorescence signal occurred. Fluorescence signals occurring when varying concentrations of urea DNA were added under the conditions selected through the experiment were measured. As can be seen in FIGS. 7(c) and 7(d), as the concentration of urea DNA increased, polymerase activity increased, and thus high fluorescence signals occurred. Furthermore, it could be seen that the fluorescence signal increased linearly in the urea DNA concentration range of 0 to 20 nM and that the detection limit was 2.67 nM.

TABLE 4

| Strand name | DNA sequence (5'→3') | SEQ ID NO |
|---|---|---|
| Urea-specific aptamer 2 | AAAT ACTG GTGA CCGT CCTA <u>CAAT GTA C AGTATTG</u> | SEQ ID NO: 14 |
| Urea-specific blocker | TAGG ACGG TCAC CAGT ATTT TTAA TGC T GATT ACTT TTGC | SEQ ID NO: 15 |
| Complimentary urea-target2 | GCAA AAGT AATC AGCA TTAA AAAT ACT G GTGA CCGT CCTA | SEQ ID NO: 16 |
| Non-complimentary Chlalmydia-target2 | AAAA GGGA TTGC AGCT TGTA GTCC TG CT TGAG AGAA CGTG | SEQ ID NO: 17 |

Example 3

Method of Detecting and Quantifying UDG in Switch-on Mode

Reaction mixtures were separately prepared as part A and part B. Part A (total volume of 20 μL), composed of 1× Taq reaction buffer (10 mM Tris-HCl, pH 8.3, 50 mM KCl, 4 mM MgCl$_2$), 500 μM dNTPs, 400 nM UDG aptamer, and 40 nM UDG blocker, was heated at 90° C. for 5 min, cooled slowly to 37° C. (0.1 ° C./sec) and incubated at 37° C. for 20 min. Then, varying concentrations of UDG, or other enzymes, including hAAG, hOGG1, Fpg, BamHI, Exo I and Lambda exonuclease, were then added to each solution and incubated at 37° C. for 30 min. The solutions incubated as described above were cooled slowly to 25° C. (0.1 ° C./sec) and incubated at 25° C. for 5 min. Then, Taq DNA polymerase (11 nM) was added to each solution and incubated for 20 min. Part B (total volume of 20 μL), composed of 1× Taq reaction buffer, 600 nM template, 600 nM primer, and 500 nM TaqMan probe, was heated at 90° C. for 5 min, cooled slowly to 25° C. (0.1° C./sec) and incubated at 25° C. for 60 min. Part A and part B were mixed with each other, and the fluorescence signal was measured on a C1000™ thermal cycler. The fluorescence signal arising from TaqMan probe during the primer extension reaction was monitored at 2-min intervals at a polymerization reaction temperature of 20 to 30° C. (preferably 25° C.). The following Experimental Examples 6 to 8 were performed according to the method of Example 3.

Experimental Example 6

FIG. 10 shows the results of testing the effect of UDG on polymerase activity using a DNA aptamer designed so as to respond specifically to UDG. Table 5 below shows the DNA sequences used in this experiment. As can be seen in FIGS. 10(a) and 10(b), only when UDG target enzyme was present, polymerase activity increased, and thus high fluorescence signals occurred (3). However, when an experiment was performed in which a DNA containing thymine in place of uracil nucleobase was introduced to a blocker DNA complementary to the single-stranded region of the DNA aptamer, it could be seen that polymerase activity was inhibited by the DNA aptamer regardless of the presence or absence of UDG (4 and 5). This suggests that the cleavage of uracil nucleobase by UDG plays an important role in the restoration of polymerase activity and that UDG enzyme activity can be detected and quantified based on the cleavage of uracil nucleobase by UDG.

Experimental Example 7

FIG. 11 shows the results of measuring fluorescence signals occurring when UDG was added at varying concentrations based on the optimal conditions determined by the experiment, as shown in FIG. 10. Table 5 above shows the DNA sequences used in this experiment (underline: conserved region). It could be seen that, as the concentration of UDG increased, polymerase activity increased, and thus high fluorescence signals occurred. Furthermore, it could be seen that the fluorescence signal increased linearly in the UDG concentration region of 0 to 0.3 U/mL and that the detection limit was 0.024 U/mL.

Experimental Example 8

FIG. 12 shows the results of testing the specificity of the newly developed system for analyzing a target enzyme. Table 5 above shows the DNA sequences used in this experiment (underline: conserved region). As could be seen from the results in FIG. 12, when hAAG (human alkyladenine DNA glycosylase) (3), hOGG1 (human 8-oxoguanine DNA glycosylase 1) (4), Fpg (formamidopyrimidine-DNA glycosylase) (5), BamHI (6), Exo I (7) or Lambda exonuclease (8) was present, the polymerase activity inhibited by the DNA aptamer was not restored, and a low fluorescence signal appeared. However, when the target enzyme UDG was present, the DNA aptamer was converted to a DNA aptamer structure containing a single strand by the cleavage of uracil nucleobase, and thus polymerase was activated and a high fluorescence signal appeared.

INDUSTRIAL APPLICABILITY

As described above, the present invention can provide a method for diagnosing biomolecules, which can detect and quantify target nucleic acids, target proteins, target small-molecular substances, target enzyme activities and the like in a label-free and sensitive manner by controlling polymerase activity through target molecule-induced conformational change of a DNA aptamer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

TABLE 5

| Strand name | DNA sequence (5'→3') | SEQ ID NO |
| --- | --- | --- |
| UDG aptamer | TTTT AA TTTT AA TTTT CAA TGT ACA GTA TTG | SEQ ID NO: 18 |
| UDG blocker | AAAA UU AAAA UU AAAA | SEQ ID NO: 19 |
| Control UDG blocker | AAAA TT AAAA TT AAAA | SEQ ID NO: 20 |

The invention claimed is:

1. A method of detecting or quantifying a target nucleic acid in switch-on mode using nucleic acid polymerase activity controlled by the target nucleic acid, said method comprising:
   (a) adding a nucleic acid polymerase and a detection sample, which is presumed to contain the target nucleic acid, to a mixture containing a blocker nucleic acid, which has a nucleotide sequence complementary to the target nucleic acid, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex;
   (b) mixing a mixture containing a primer and a signal-generating substance with the reaction product of step (a), followed by a primer extension reaction; and
   (c) analyzing the primer extension reaction of step (b) to thereby detect or quantify the target nucleic acid,
   wherein the aptamer has a conserved region represented by SEQ ID NO: 21 at its 5' terminus or 3' terminus, and
   wherein the mixture containing the signal-generating substance further contains a template nucleic acid and a TaqMan probe.

2. The method of claim 1, wherein the single strand of the aptamer has a nucleotide sequence complementary to the blocker nucleic acid.

3. The method of claim 1, wherein the aptamer forms a stable structure upon binding to the blocker nucleic acid, and then binds to the nucleic acid polymerase to reduce the activity of the polymerase.

4. The method of claim 1, wherein the aptamer has a nucleotide sequence represented by SEQ ID NO: 14.

5. The method of claim 1, wherein the target nucleic acid is either complementary urea-target 2 (SEQ ID NO: 16) or non-complementary chlamydia-target 2 (SEQ ID NO: 17).

6. The method of claim 1, wherein the nucleic acid polymerase is Taq DNA polymerase.

7. The method of claim 1, wherein the primer extension reaction is performed at a temperature of 20 to 30° C.

8. The method of claim 1, wherein the signal-generating substance is labeled with a substance selected from the group consisting of radioisotopes, fluorescent substances, dyes, nanoparticles, enzymes, enzymatic substrates, luminescent substances, and substances containing an electrochemical functional group.

9. The method of claim 1, wherein step (c) comprises detecting or quantifying a signal derived from the primer extension reaction of step (b) to thereby determine the presence or absence of the target nucleic acid.

10. The method of claim 1, wherein the blocker nucleic acid is a urea-specific blocker having a nucleotide sequence represented by SEQ ID NO: 15.

11. A method of detecting or quantifying a target molecule in switch-on mode using nucleic acid polymerase activity controlled by the target molecule, said method comprising:
    (a) adding a nucleic acid polymerase and a detection sample, which is presumed to contain the target molecule, to a mixture containing a blocker nucleic acid having a nucleotide sequence which specifically recognizes and binds to the target molecule, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex;
    (b) mixing a mixture containing a primer and a signal-generating substance with the reaction product of step (a), followed by a primer extension reaction; and
    (c) analyzing the primer extension reaction of step (b) to thereby detect or quantify the target molecule,
    wherein the aptamer has a conserved region represented by SEQ ID NO: 21 at its 5' terminus or 3' terminus, and
    wherein the mixture containing the signal-generating substance further contains a template nucleic acid and a TaqMan probe.

12. The method of claim 11, wherein the single strand of the aptamer has a nucleotide sequence complementary to the blocker nucleic acid.

13. The method of claim 11, wherein the aptamer forms a stable structure upon binding to the blocker nucleic acid, and then binds to the nucleic acid polymerase to reduce the activity of the polymerase.

14. The method of claim 11, wherein the target molecule is any one selected from the group consisting of a nucleic acid, a carbohydrate, a lipid, a protein, a peptide, an aptamer, an antigen, an antibody, a hapten, a low-molecular-weight material, a macromolecular complex, a cell, a pharmaceutical agent, an organic compound, and an inorganic compound.

15. The method of claim 11, wherein the nucleic acid polymerase is Taq DNA polymerase.

16. The method of claim 11, wherein the primer extension reaction is performed at a temperature of 20 to 30° C.

17. The method of claim 11, wherein the signal-generating substance is labeled with a substance selected from the group consisting of radioisotopes, fluorescent substances, dyes, nanoparticles, enzymes, enzymatic substrates, luminescent substances, and substances containing an electrochemical functional group.

18. The method of claim 11, wherein step (c) comprises detecting or quantifying a signal derived from the primer extension reaction of step (b) to thereby determine the presence or absence of the target nucleic acid.

19. A method of detecting or quantifying target BER (Base Excision Repair) enzyme activity in switch-on mode using nucleic acid polymerase activity controlled by BER (Base Excision Repair) enzyme, said method comprising:
(a) adding a nucleic acid polymerase and a detection sample, which is presumed to contain the target BER enzyme, to a mixture containing a blocker nucleic acid, which has a nucleotide sequence specific for the target BER enzyme, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex;
(b) mixing a mixture containing a primer and a signal-generating substance with the reaction product of step (a), followed by a primer extension reaction; and
(c) analyzing the primer extension reaction of step (b) to thereby detect or quantify the activity of the target BER (Base Excision Repair) enzyme,
wherein the aptamer has a conserved region represented by SEQ ID NO: 21 at its 5' terminus or 3' terminus, and
wherein the mixture containing the signal-generating substance further contains a template nucleic acid and a TaqMan probe.

20. The method of claim 19, wherein the single strand of the aptamer has a nucleotide sequence complementary to the blocker nucleic acid.

21. The method of claim 19, wherein the aptamer forms a stable structure upon binding to the blocker nucleic acid, and then binds to the nucleic acid polymerase to reduce the activity of the polymerase.

22. The method of claim 19, wherein the aptamer has a nucleotide sequence represented by SEQ ID NO: 18.

23. The method of claim 19, wherein the blocker nucleic acid is a UDG (uracil DNA glycosylase) blocker having a nucleotide sequence represented by SEQ ID NO: 19, which is used as a substrate for the target BER enzyme.

24. The method of claim 19, wherein the target BER enzyme is a UDG (uracil DNA glycosylase).

25. The method of claim 19, wherein the nucleic acid polymerase is Taq DNA polymerase.

26. The method of claim 19, wherein the primer extension reaction is performed at a temperature of 20 to 30° C.

27. The method of claim 19, wherein the signal-generating substance is labeled with a substance selected from the group consisting of radioisotopes, fluorescent substances, dyes, nanoparticles, enzymes, enzymatic substrates, luminescent substances, and substances containing an electrochemical functional group.

28. The method of claim 19, wherein step (c) comprises detecting or quantifying a signal derived from the primer extension reaction of step (b) to thereby analyze the activity of the target BER (Base Excision Repair) enzyme.

29. A method of detecting or quantifying target nuclease activity in switch-on mode using nucleic acid polymerase activity controlled by target nuclease, said method comprising:
(a) adding a nucleic acid polymerase and a detection sample, which is presumed to contain the target nuclease, to a mixture containing a blocker nucleic acid, which has a nucleotide sequence specific for the target nuclease, and an aptamer comprising a single-stranded nucleic acid complementary to the blocker nucleic acid, and reacting the nucleic acid polymerase and the detection sample with the mixture to thereby bind the nucleic acid polymerase to an aptamer-blocker nucleic acid complex;
(b) mixing a mixture containing a primer and a signal-generating substance to the reaction product of step (a), followed by a primer extension reaction; and
(c) analyzing the primer extension reaction of step (b) to thereby detect or quantify the target nuclease activity,
wherein the aptamer has a conserved region represented by SEQ ID NO: 21 at its 5' terminus or 3' terminus, and
wherein the mixture containing the signal-generating substance further contains a template nucleic acid and a TaqMan probe.

30. The method of claim 29, wherein the single strand of the aptamer has a nucleotide sequence complementary to the blocker nucleic acid.

31. The method of claim 29, wherein the aptamer forms a stable structure upon binding to the blocker nucleic acid, and then binds to the nucleic acid polymerase to reduce the activity of the polymerase.

32. The method of claim 29, wherein the nucleic acid polymerase is Taq DNA polymerase.

33. The method of claim 29, wherein the primer extension reaction is performed at a temperature of 20 to 30° C.

34. The method of claim 29, wherein the signal-generating substance is labeled with a substance selected from the group consisting of radioisotopes, fluorescent substances, dyes, nanoparticles, enzymes, enzymatic substrates, luminescent substances, and substances containing an electrochemical functional group.

35. The method of claim 29, wherein step (c) comprises detecting or quantifying a signal derived from the primer extension reaction of step (b) to thereby analyze the activity of the target nucleic acid enzyme.

36. The method of claim 1, wherein the mixture of step (a) is heated at about 90° C. for about 5 minutes, and then cooled slowly to about 25° C., after which the nucleic acid polymerase is added thereto and reacted.

37. The method of claim 1, wherein the mixture containing the signal-generating substance, used in step (b), is heated at about 90° C. for about 5 minutes, and then cooled slowly to about 25° C., after which it is subjected to a reaction that binds the primer and a TaqMan probe to a template nucleic acid, and then mixed with the reaction product of step (a).

38. The method of claim 1, wherein the blocker nucleic acid is either a blocker DNA or a blocker RNA.

39. The method of claim 11, wherein the blocker nucleic acid is a DNA or RNA which specifically recognizes and binds to the target molecule.

40. The method of claim 19, wherein the blocker nucleic acid is a DNA which is used as a substrate for the target BER enzyme.

41. The method of claim 19, wherein the mixture of step (a) is heated at about 90° C. for about 5 minutes, and then cooled slowly to about 37° C., after which the detection sample, which is presumed to contain the target BER (Base Excision Repair) enzyme, is added thereto and the resultant mixture is cooled slowly to about 25° C., after which a target nucleic acid polymerase is added thereto and reacted.

42. The method of claim 19, wherein the mixture containing the signal-generating substance of step (b) is heated at about 90° C. for about 5 minutes, and then cooled slowly to about 25° C., followed by a reaction that binds a primer and a TaqMan probe to the template and then is mixed with the reaction product of step (a).

43. The method of claim 29, wherein the blocker nucleic acid is a DNA or RNA which is used as a substrate for the target nuclease.

\* \* \* \* \*

SEQUENCE LISTING

<160> NUMBER OF SEQ ID NOS: 21

<210> SEQ ID NO 1
<211> LENGTH: 78
<212> TYPE: DNA
<213> ORGANISM: Artificial Sequence
<220> FEATURE:
<223> OTHER INFORMATION: Original DNA aptamer

<400> SEQUENCE: 1
ttctcggttg gtctctggcg gagcaagacc agacaatgta cagtattggc ctgatcttgt    60
gtatgattcg cttttccc                                                 78

<210> SEQ ID NO 2
<211> LENGTH: 35
<212> TYPE: DNA
<213> ORGANISM: Artificial Sequence
<220> FEATURE:
<223> OTHER INFORMATION: T20-aptamer

<400> SEQUENCE: 2
tttttttttt tttttttttt caatgtacag tattg                              35

<210> SEQ ID NO 3
<211> LENGTH: 20
<212> TYPE: DNA
<213> ORGANISM: Artificial Sequence
<220> FEATURE:
<223> OTHER INFORMATION: A20-target

<400> SEQUENCE: 3
aaaaaaaaaa aaaaaaaaaa                                               20

<210> SEQ ID NO 4
<211> LENGTH: 35
<212> TYPE: DNA
<213> ORGANISM: Artificial Sequence
<220> FEATURE:
<223> OTHER INFORMATION: Random1-aptamer

<400> SEQUENCE: 4
agtcagtcag tcagtcagtc caatgtacag tattg                              35

<210> SEQ ID NO 5
<211> LENGTH: 20
<212> TYPE: DNA
<213> ORGANISM: Artificial Sequence
<220> FEATURE:
<223> OTHER INFORMATION: Random1-target

<400> SEQUENCE: 5
gactgactga ctgactgact                                               20

<210> SEQ ID NO 6
<211> LENGTH: 35
<212> TYPE: DNA
<213> ORGANISM: Artificial Sequence
<220> FEATURE:
<223> OTHER INFORMATION: Random2-aptamer

<400> SEQUENCE: 6
actgactgac tgactgactg caatgtacag tattg                              35

```
<210> SEQ ID NO 7
<211> LENGTH: 20
<212> TYPE: DNA
<213> ORGANISM: Artificial Sequence
<220> FEATURE:
<223> OTHER INFORMATION: Random2-target

<400> SEQUENCE: 7
cagtcagtca gtcagtcagt                                                  20

<210> SEQ ID NO 8
<211> LENGTH: 35
<212> TYPE: DNA
<213> ORGANISM: Artificial Sequence
<220> FEATURE:
<223> OTHER INFORMATION: T20-aptamer (Reverse)

<400> SEQUENCE: 8
caatgtacag tattgttttt tttttttttt ttttt                                 35

<210> SEQ ID NO 9
<211> LENGTH: 40
<212> TYPE: DNA
<213> ORGANISM: Artificial Sequence
<220> FEATURE:
<223> OTHER INFORMATION: Urea-specific aptamer 1

<400> SEQUENCE: 9
taggacggtc accagtattt ttaatcaatg tacagtattg                            40

<210> SEQ ID NO 10
<211> LENGTH: 25
<212> TYPE: DNA
<213> ORGANISM: Artificial Sequence
<220> FEATURE:
<223> OTHER INFORMATION: Complementary urea-target 1

<400> SEQUENCE: 10
attaaaaata ctggtgaccg tccta                                            25

<210> SEQ ID NO 11
<211> LENGTH: 25
<212> TYPE: DNA
<213> ORGANISM: Artificial Sequence
<220> FEATURE:
<223> OTHER INFORMATION: Non-complementary Chlamydia-target 1

<400> SEQUENCE: 11
atcttaaaag ggattgcagc ttgta                                            25

<210> SEQ ID NO 12
<211> LENGTH: 40
<212> TYPE: DNA
<213> ORGANISM: Artificial Sequence
<220> FEATURE:
<223> OTHER INFORMATION: Chlamydia-specific aptamer

<400> SEQUENCE: 12
tacaagctgc aatccctttt aagatcaatg tacagtattg                            40

<210> SEQ ID NO 13
<211> LENGTH: 25
<212> TYPE: DNA
<213> ORGANISM: Artificial Sequence
<220> FEATURE:
<223> OTHER INFORMATION: Complementary Chlamydia-target
```

```
<400> SEQUENCE: 13
atcttaaaag ggattgcagc ttgta                                     25

<210> SEQ ID NO 14
<211> LENGTH: 35
<212> TYPE: DNA
<213> ORGANISM: Artificial Sequence
<220> FEATURE:
<223> OTHER INFORMATION: Urea-specific aptamer2

<400> SEQUENCE: 14
aaatactggt gaccgtccta caatgtacag tattg                          35

<210> SEQ ID NO 15
<211> LENGTH: 40
<212> TYPE: DNA
<213> ORGANISM: Artificial Sequence
<220> FEATURE:
<223> OTHER INFORMATION: Urea-specific blocker

<400> SEQUENCE: 15
taggacggtc accagtattt ttaatgctga ttactttgc                      40

<210> SEQ ID NO 16
<211> LENGTH: 40
<212> TYPE: DNA
<213> ORGANISM: Artificial Sequence
<220> FEATURE:
<223> OTHER INFORMATION: Complementary urea-target

<400> SEQUENCE: 16
gcaaaagtaa tcagcattaa aaatactggt gaccgtccta                     40

<210> SEQ ID NO 17
<211> LENGTH: 40
<212> TYPE: DNA
<213> ORGANISM: Artificial Sequence
<220> FEATURE:
<223> OTHER INFORMATION: Non-complementary Chlamydia-target

<400> SEQUENCE: 17
aaaagggatt gcagcttgta gtcctgcttg agagaacgtg                     40

<210> SEQ ID NO 18
<211> LENGTH: 31
<212> TYPE: DNA
<213> ORGANISM: Artificial Sequence
<220> FEATURE:
<223> OTHER INFORMATION: UDG aptamer

<400> SEQUENCE: 18 ttttaattt aattttcaat gtacagtatt g                               31

<210> SEQ ID NO 19
<211> LENGTH: 16
<212> TYPE: RNA
<213> ORGANISM: Artificial Sequence
<220> FEATURE:
<223> OTHER INFORMATION: UDG blocker

<400> SEQUENCE: 19
aaaauuaaaa uuaaaa                                               16
```

```
<210> SEQ ID NO 20
<211> LENGTH: 16
<212> TYPE: DNA
<213> ORGANISM: Artificial Sequence
<220> FEATURE:
<223> OTHER INFORMATION: Control UDG blocker

<400> SEQUENCE: 20
aaaattaaaa ttaaaa                                              16

<210> SEQ ID NO 21
<211> LENGTH: 15
<212> TYPE: DNA
<213> ORGANISM: Artificial Sequence
<220> FEATURE:
<223> OTHER INFORMATION: Conserved region of aptamer

<400> SEQUENCE: 21
caatgtacag tattg                                               15
```